(12) United States Patent
Schwartz et al.

(10) Patent No.: US 12,376,978 B2
(45) Date of Patent: ***Aug. 5, 2025

(54) METHODS AND TECHNOLOGY FOR CREATING CONNECTIONS AND SHUNTS BETWEEN VESSELS AND CHAMBERS OF BIOLOGIC STRUCTURES

(71) Applicant: NXT Biomedical, LLC, Irvine, CA (US)

(72) Inventors: Robert S. Schwartz, Inver Grove Heights, MN (US); Stanton J. Rowe, Newport Coast, CA (US); Robert C. Taft, Orange, CA (US); Glen Rabito, Lake Forest, CA (US); Alexander Siegel, Aliso Viejo, CA (US); Joseph Passman, Costa Mesa, CA (US)

(73) Assignee: NXT Biomedical, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/334,302

(22) Filed: Jun. 13, 2023

(65) Prior Publication Data

US 2023/0320877 A1 Oct. 12, 2023

Related U.S. Application Data

(63) Continuation of application No. 16/576,704, filed on Sep. 19, 2019, now Pat. No. 11,717,429.

(Continued)

(51) Int. Cl.
*A61F 2/06* (2013.01)
*A61B 17/00* (2006.01)

(Continued)

(52) U.S. Cl.
CPC ............. *A61F 2/958* (2013.01); *A61F 2/82* (2013.01); *A61F 2/9522* (2020.05)

(58) Field of Classification Search
None
See application file for complete search history.

(56) References Cited

U.S. PATENT DOCUMENTS 5,584,803 A * 12/1996 Stevens ............. A61F 2/2433
604/6.16
5,895,404 A * 4/1999 Ruiz ................. A61B 17/11
600/11

(Continued)

FOREIGN PATENT DOCUMENTS

JP 2000-505316 A 5/2000
JP 2002-516696 A 6/2002

(Continued)

OTHER PUBLICATIONS

Japanese Patent Office, Office Action dated Sep. 19, 2023 with English translation in Japanese Patent Application No. 2021-515145, 8 pages.

(Continued)

*Primary Examiner* — Ann Hu
(74) *Attorney, Agent, or Firm* — Inskeep IP Group, Inc.

(57) ABSTRACT

Devices and methods of treating conditions cause or exacerbated by excessive fluid pressures or retentions, such as pulmonary hypertension, that involves shunting excessive fluid pressure from one bodily chamber or vessel to another bodily chamber or vessel.

13 Claims, 36 Drawing Sheets

Related U.S. Application Data

(60) Provisional application No. 62/802,656, filed on Feb. 7, 2019, provisional application No. 62/779,380, filed on Dec. 13, 2018, provisional application No. 62/747,649, filed on Oct. 18, 2018, provisional application No. 62/733,533, filed on Sep. 19, 2018.

(51) Int. Cl.
*A61B 17/11* (2006.01)
*A61F 2/82* (2013.01)
*A61F 2/958* (2013.01)
*A61M 25/00* (2006.01)
*A61F 2/95* (2013.01)

(56) References Cited

U.S. PATENT DOCUMENTS

| | | | | |
|---|---|---|---|---|
| 6,344,022 | B1* | 2/2002 | Jarvik | A61M 1/3653 623/3.16 |
| 6,395,212 | B1* | 5/2002 | Solem | A61F 2/07 264/230 |
| 6,669,708 | B1* | 12/2003 | Nissenbaum | A61B 17/11 606/151 |
| 6,935,344 | B1* | 8/2005 | Aboul-Hosn | A61M 1/3653 128/898 |
| 7,628,768 | B2 | 12/2009 | Faul et al. | |
| 7,967,769 | B2 | 6/2011 | Faul et al. | |
| 8,048,016 | B2 | 11/2011 | Faul et al. | |
| 8,449,443 | B2* | 5/2013 | Rodefeld | A61M 60/135 600/16 |
| 8,574,185 | B2 | 11/2013 | Faul et al. | |
| 10,357,637 | B2* | 7/2019 | Klepetko | A61M 1/3659 |
| 11,717,429 | B2* | 8/2023 | Schwartz | A61M 60/882 606/8 |
| 2002/0128587 | A1* | 9/2002 | Aboul-Hosn | A61M 60/414 604/7 |
| 2003/0040736 | A1* | 2/2003 | Stevens | A61M 25/0041 604/100.01 |
| 2003/0187322 | A1 | 10/2003 | Siess | |
| 2004/0093067 | A1 | 5/2004 | Israel | |
| 2010/0222869 | A1* | 9/2010 | Delaney | A61F 2/06 623/1.34 |
| 2011/0218479 | A1 | 9/2011 | Rottenberg et al. | |
| 2011/0257462 | A1* | 10/2011 | Rodefeld | A61F 2/06 600/16 |
| 2013/0030521 | A1* | 1/2013 | Nitzan | A61F 2/2412 623/2.13 |
| 2013/0178783 | A1 | 7/2013 | McNamara et al. | |
| 2013/0178784 | A1 | 7/2013 | McNamara et al. | |
| 2015/0057687 | A1* | 2/2015 | Gittard | A61B 17/11 606/153 |
| 2017/0071722 | A1 | 3/2017 | Rafiee | |
| 2018/0221632 | A1 | 8/2018 | Scheule et al. | |
| 2020/0306432 | A1* | 10/2020 | Pekkan | A61M 60/152 |

FOREIGN PATENT DOCUMENTS

| | | |
|---|---|---|
| JP | 2002-524196 A | 8/2002 |
| JP | 2007-296375 A | 11/2007 |
| JP | 2011-509151 A | 3/2011 |
| JP | 2013-539666 A | 10/2013 |
| JP | 2017-513602 A | 6/2017 |
| WO | WO 1997/027898 A1 | 8/1997 |
| WO | WO 1999/062415 A1 | 12/1999 |
| WO | WO 2000/015147 A1 | 3/2000 |
| WO | WO 2000/015148 A1 | 3/2000 |
| WO | WO 2005/020848 A2 | 3/2005 |
| WO | WO 2009/089055 A1 | 7/2009 |
| WO | WO 2012/034108 A1 | 3/2012 |
| WO | WO 2015/168504 A2 | 11/2015 |

OTHER PUBLICATIONS

Japanese Patent Office, Decision of Refusal dated Mar. 12, 2024 with English translation in Japanese Patent Application No. 2021-515145, 10 pages.

WIPO, U.S. International Search Authority, International Search Report and Written Opinion mailed Dec. 6, 2019 in International Patent Application No. PCT/US2019/052025, 10 pages.

China Patent Office, Office Action dated Jul. 28, 2022 with English translation in Chinese Patent Application No. 201980073629.X, 13 pages.

* cited by examiner

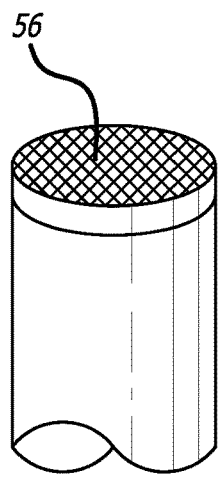 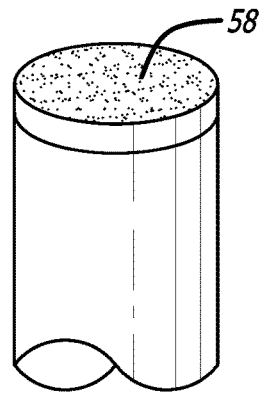
FIG. 14  FIG. 15
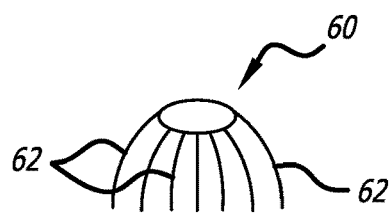 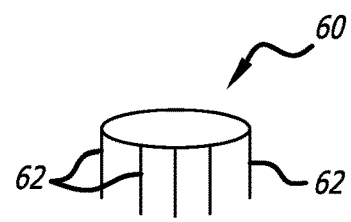
FIG. 16  FIG. 17
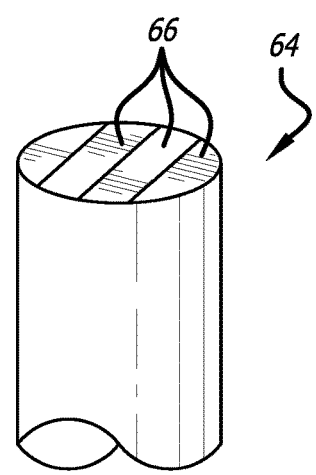 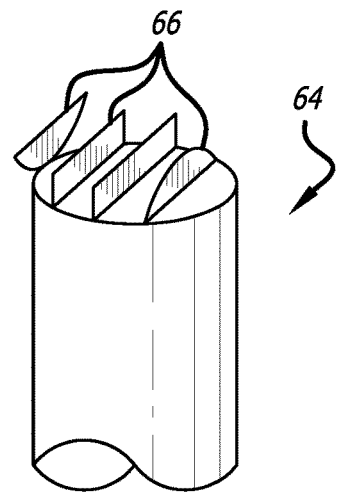
FIG. 18  FIG. 19

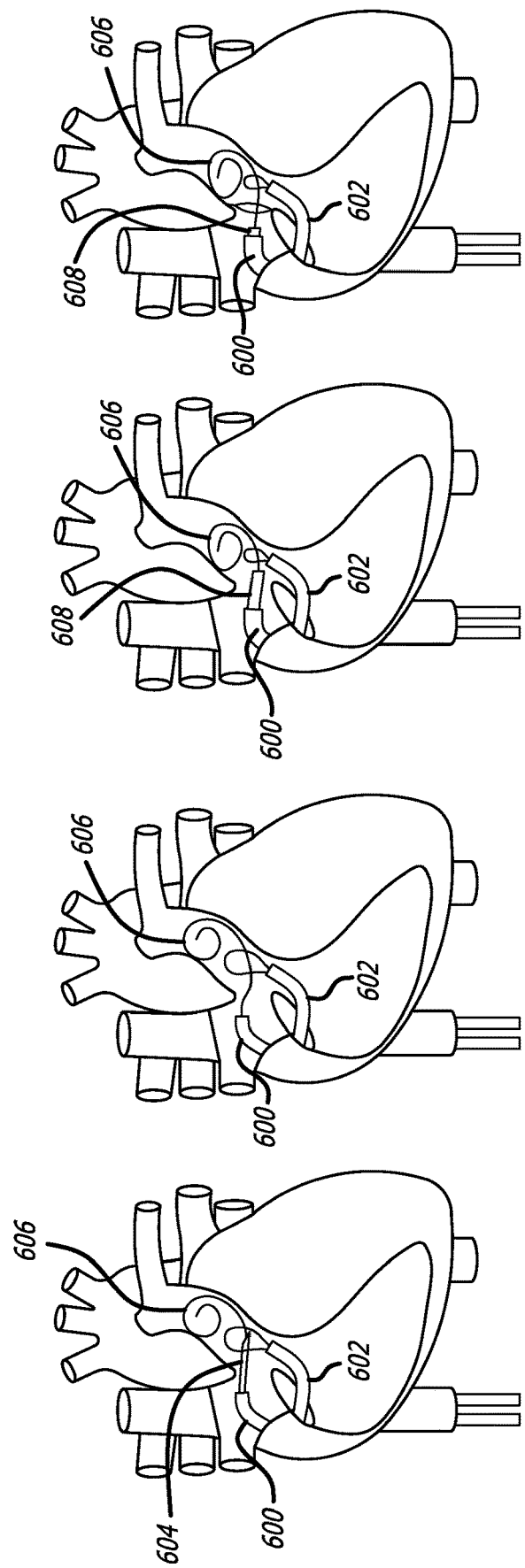

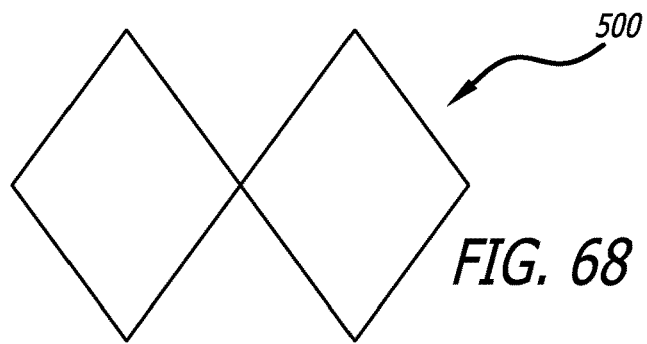
FIG. 68
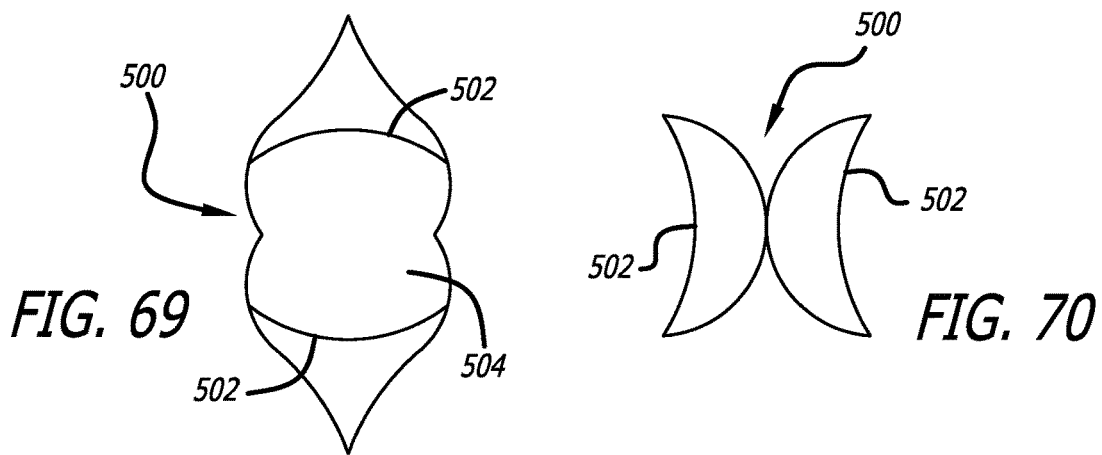
FIG. 69
FIG. 70
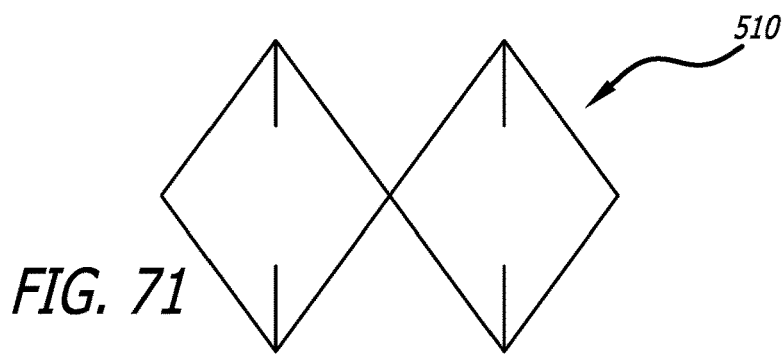
FIG. 71
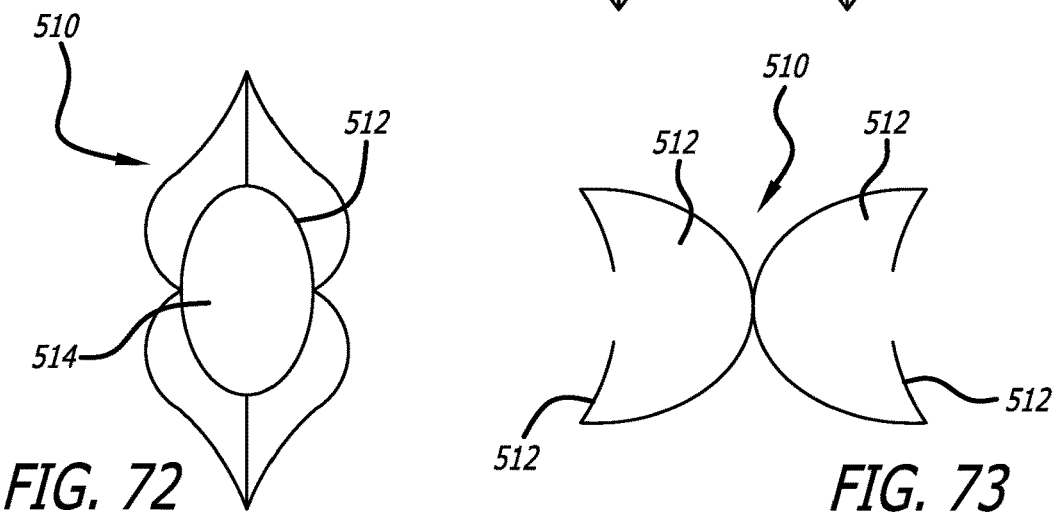
FIG. 72
FIG. 73

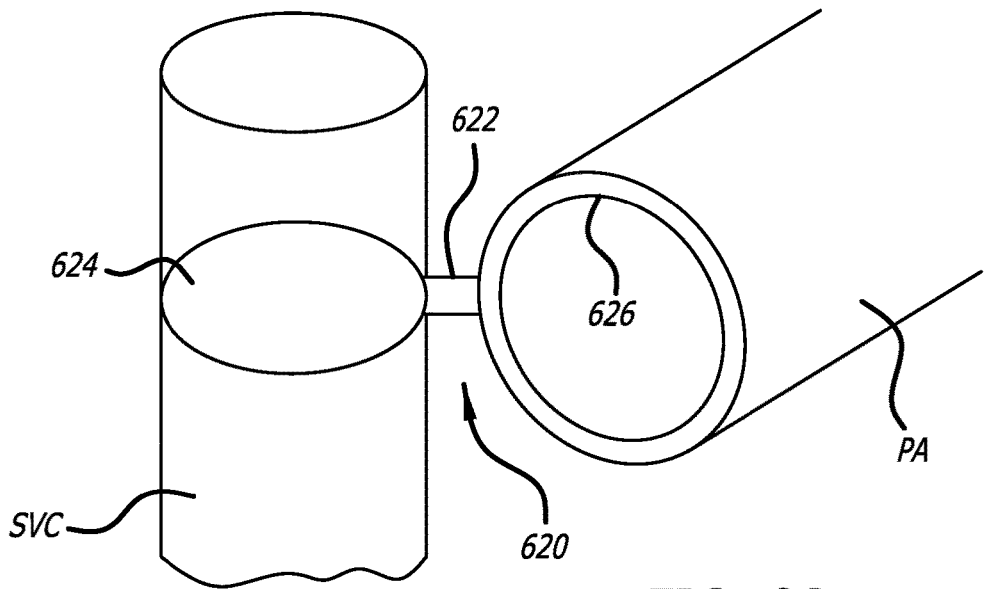
FIG. 83
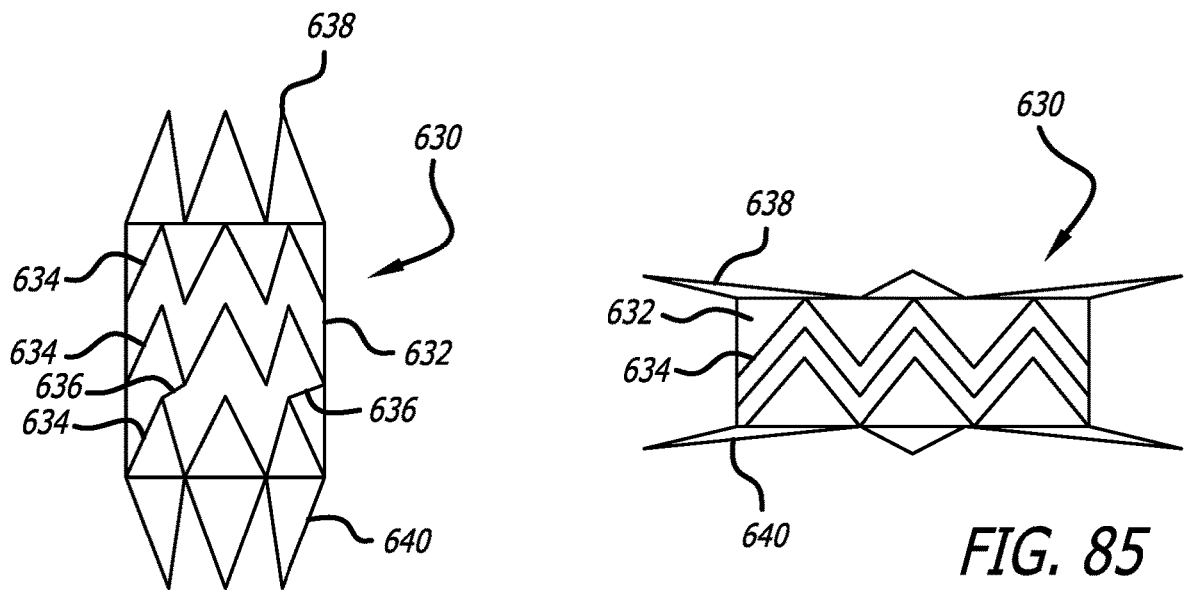
FIG. 84
FIG. 85

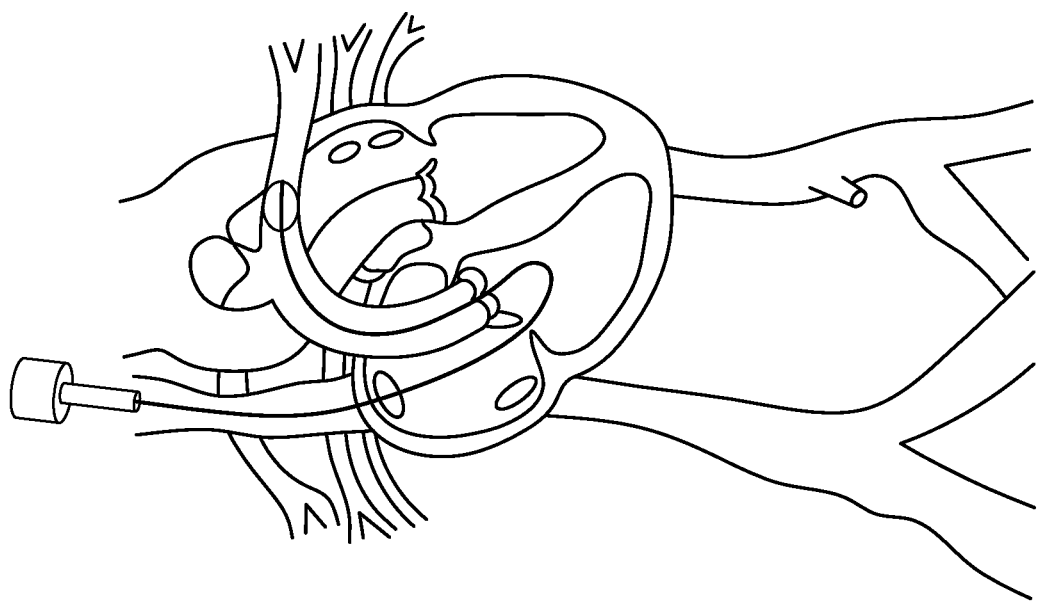
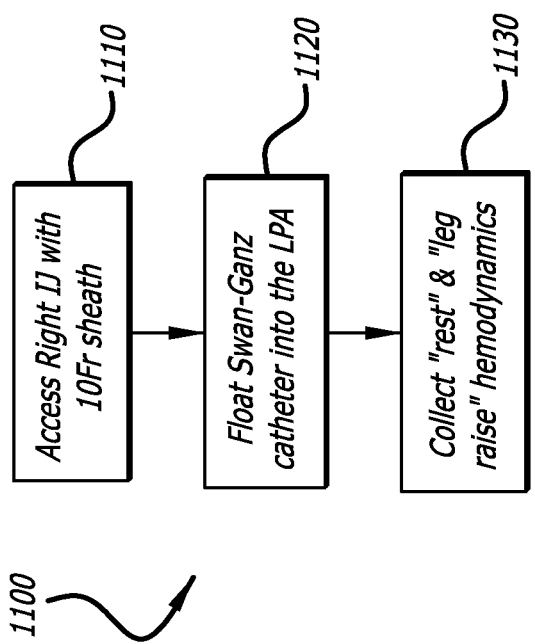
FIG. 100

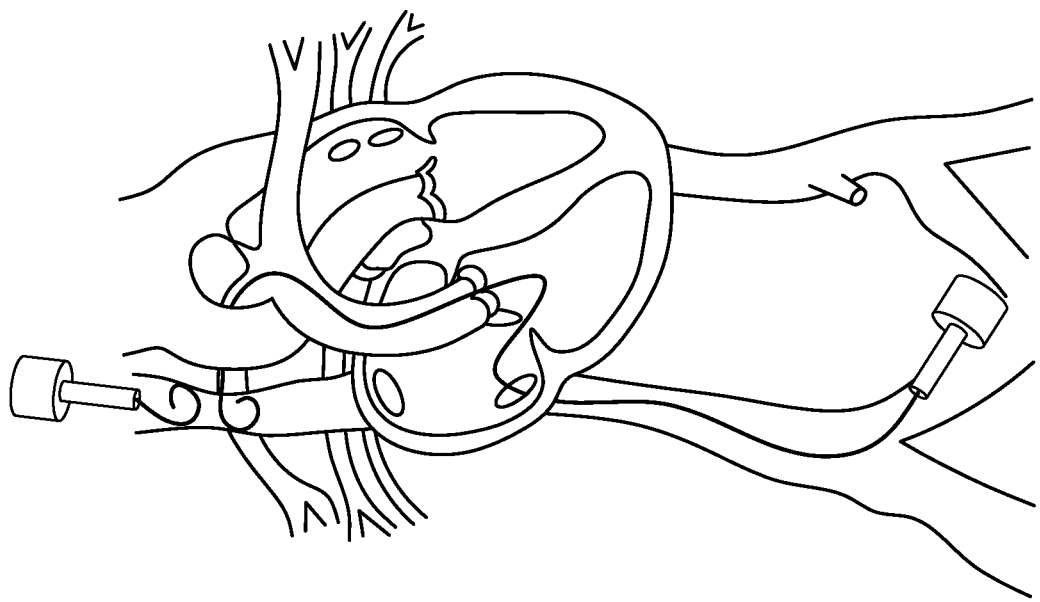
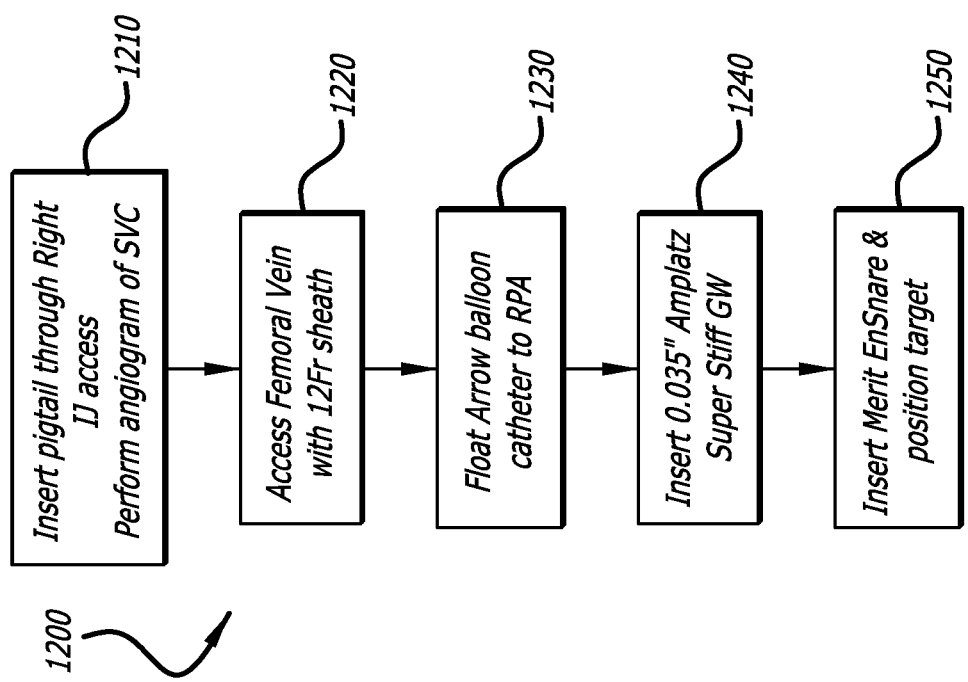
FIG. 101

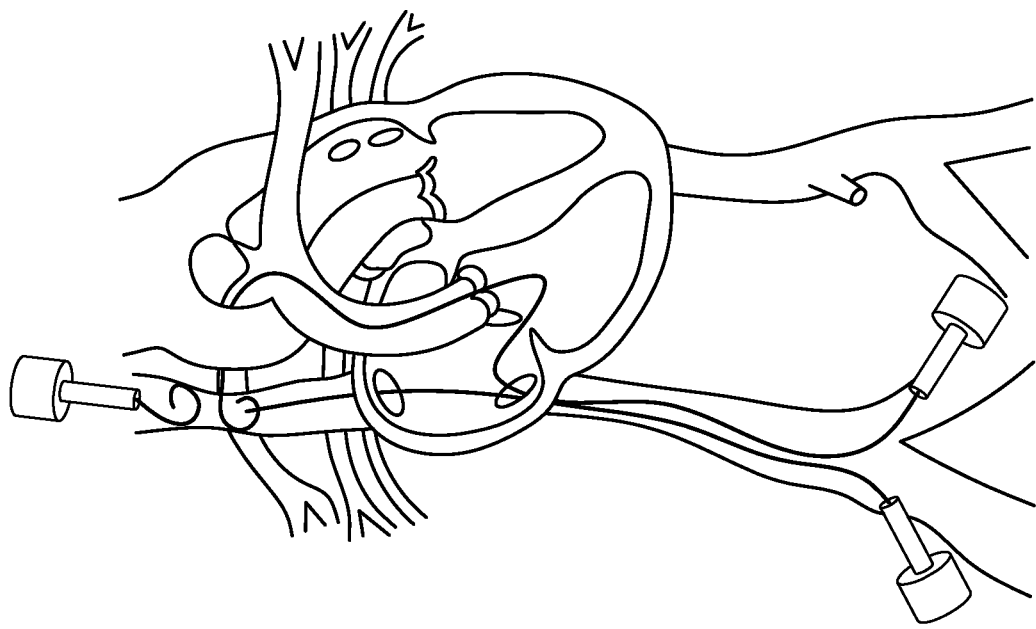
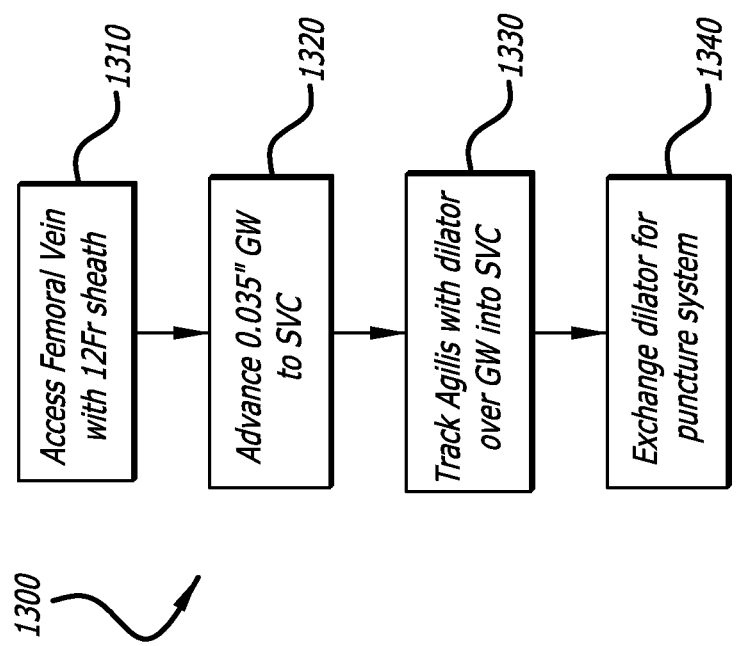
FIG. 102

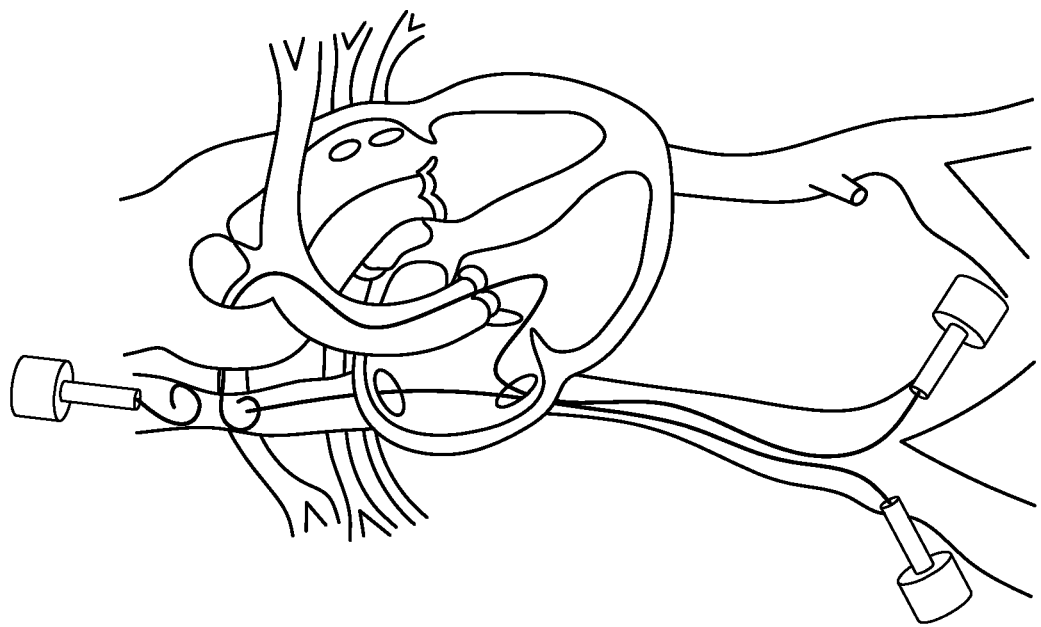
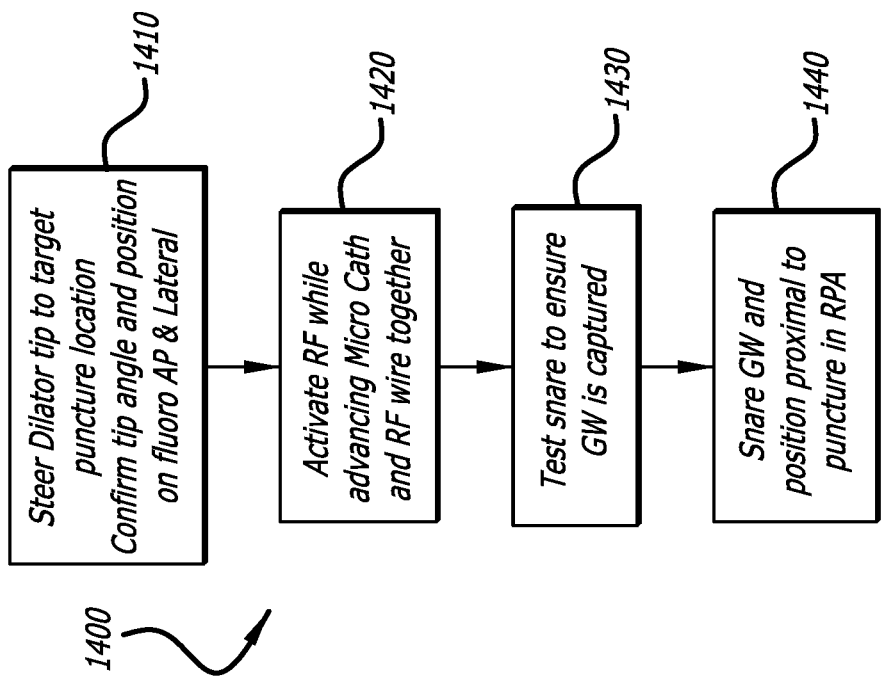
FIG. 103

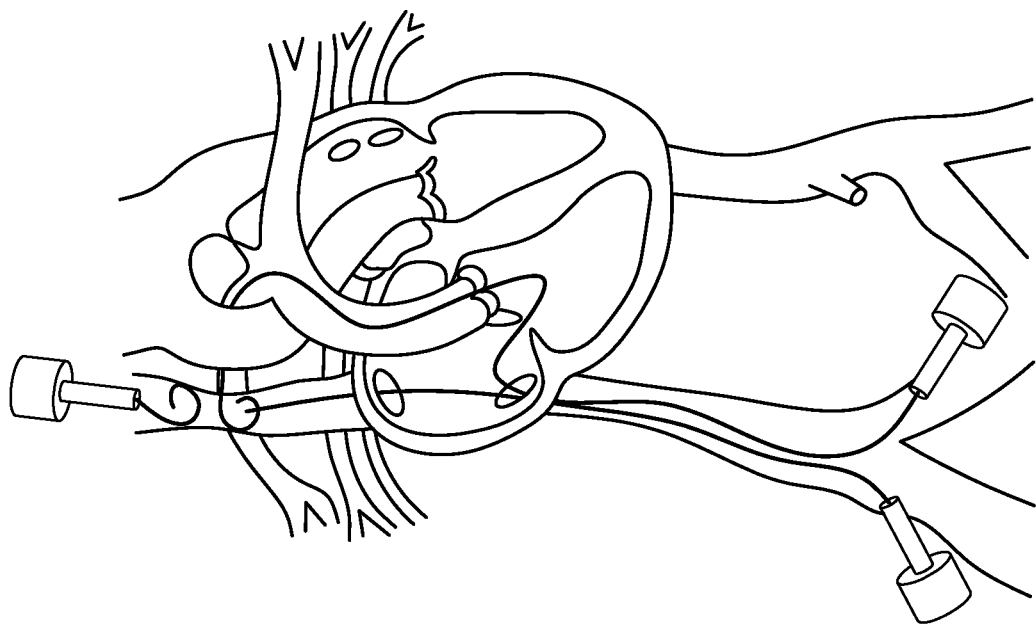
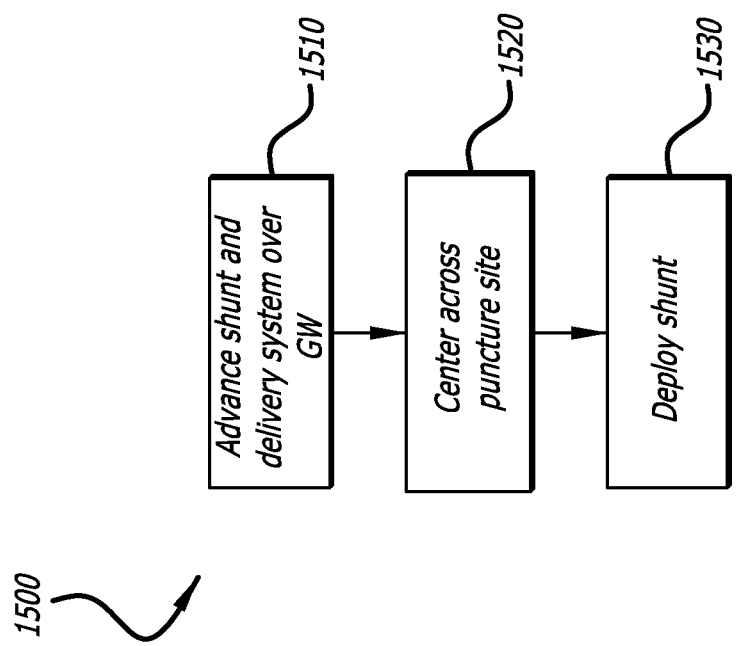
FIG. 104

METHODS AND TECHNOLOGY FOR CREATING CONNECTIONS AND SHUNTS BETWEEN VESSELS AND CHAMBERS OF BIOLOGIC STRUCTURES

RELATED APPLICATIONS

This application is a continuation of and claims priority to U.S. patent application Ser. No. 16/576,704 filed Sep. 19, 2019 entitled Methods And Technology For Creating Connections And Shunts Between Vessels And Chambers Of Biologic Structures; which claims benefit of and priority to U.S. Provisional Application Ser. No. 62/733,533 filed Sep. 19, 2018 entitled Methods And Technology For Creating Connections And Shunts Between Vessels And Chambers Of Biologic Structures; and to U.S. Provisional Application Ser. No. 62/747,649 filed Oct. 18, 2018 entitled Methods And Technology For Creating Connections And Shunts Between Vessels And Chambers Of Biologic Structures; and to U.S. Provisional Application Ser. No. 62/779,380 filed Dec. 13, 2018 entitled Methods And Technology For Creating Connections And Shunts Between Vessels And Chambers Of Biologic Structures; and to U.S. Provisional Application Ser. No. 62/802,656 filed Feb. 7, 2019, entitled Methods And Technology For Creating Connections And Shunts Between Vessels And Chambers Of Biologic Structures; all of which are hereby incorporated herein by reference in their entireties.

FIELD OF THE INVENTION

The present invention pertains to methods and devices for treating various medical conditions by creating fluid connections between bodily chambers or vessels that are not naturally connected.

BACKGROUND OF THE INVENTION

Pulmonary Hypertension is a condition that describes high blood pressure in the lungs. There are a variety of causes for the increased pulmonary blood pressure, including obstruction of the small arteries in the lung, high left-sided heart pressures, and chronic lung disease.

There are many medical conditions that also create high pulmonary blood pressure as a secondary condition, including heart failure. In heart failure, the heart is unable to meet the demand for blood coming from the body. This often leads to increased pressures within the heart that can back up into the lungs causing pulmonary hypertension at rest or during exercise.

In all cases, this increased pulmonary blood pressure causes the right ventricle (RV) to work harder to supply the lungs and the left side of the heart with blood. Over time, this additional load causes damage to the heart, decreasing efficiency and limiting the ability to keep up with the demands of the body, especially during exercise.

Reducing pulmonary blood pressure has been the target of numerous therapies, especially in patients with pulmonary arterial hypertension (PAH) where several drugs have shown moderate success. However, these drugs are often very expensive and burdensome to the patient and over time can lose their effectiveness.

In this regard, what is needed is an improved treatment option for reducing pulmonary blood pressure and other conditions of elevated blood pressure.

OBJECTS AND SUMMARY OF THE INVENTION

The present application is directed to additional methods and embodiments that take advantage of the surprising positive results attained practicing the methods and using the device taught therein.

Biologic and medical devices may yield therapeutic effects by creating connections or shunts between bodily chambers or vessels which are not normally connected. These shunts may be useful for altering abnormal pressures, abnormal flows, or increasing the quantity or quality of substances such as blood, lymph, or other bodily fluids including air or gases.

One aspect of the invention provides several embodiments of a device or devices for making a connection between two bodily chambers. In one or more embodiments, the device or devices for connecting such chambers/vessels have the capability of anchoring themselves within each of the chambers to be connected, compressing or pressing walls of these chambers together to create a seal preventing leakage of internal fluids, and creating a connection which permits flow of fluids or gases from one chamber to the other based upon pressure differential, flow differential or other patterns related to the physics of flow.

Another aspect provides a device that may connect two bodily chambers each with walls by a shunt/hole that is made discrete and variable size. This may entail one or more devices, connecting a chamber to a vessel (as in a heart ventricle to a great artery). Multiple permutations are feasible with this paradigm. The heart has a multiplicity of both chambers and vessels and therapeutic effects may be generated by connecting one to the other, or multiple trans-chamber/trans ventricular connections. As used herein, "bodily chamber" can mean any space or cavity in the body in which fluid or gas resides or is contained. Chambers may include, but are not limited to, cavities such as those of the heart, brain, lungs, liver, kidneys, bladder, gut or peritoneal cavity. "Vessels" generally lead to or flow from other organs or chambers and include, but are not limited to, arteries, veins, lymphatic channels, airways, ureters and the like.

One aspect of the invention provides a method of relieving pressure in a first area of the body comprising creating a shunt between the first area and a second area having a lower pressure than the first area wherein the first and second areas are not connected prior to creating the shunt. The shunt could allow a flow rate of between 0.1 L/min and 3.0 L/min, for example.

In some embodiments the first and second areas are flush with each other prior to creating the shunt. In other embodiments the first and second areas are spaced apart prior to creating the shunt. In still other embodiments, the first and second areas are spaced apart prior to and after creating said shunt.

In some embodiments the lumen includes a flow control mechanism. The flow may be the lumen and the lumen may be non-cylindrical. In one aspect the lumen is "H" shaped and expands when subjected to increased pressure.

One aspect provides a flow control mechanism that is an adaptive flow control mechanism.

In some embodiments the first and second areas are bodily chambers. In some embodiments the first and second areas are vessels.

One aspect of the invention connects a superior vena cava to a pulmonary artery.

Another aspect connects a right atrium or atrial appendage and a pulmonary artery.

Yet another aspect provides a device for creating a shunt between a first area and a second area having a lower pressure than the first area wherein the first and second areas are not connected prior to creating the shunt. The device may include a stent having a first end and a second end and a lumen extending between the first end and the second end.

The device may include a first anchoring feature at the first end and a second anchoring feature at the second end. At least one of the anchoring features may be a flange, and the flange may be self-expanding. Alternatively or additionally, the anchoring feature may be an outward radial force placed on the implantation site by the sent.

Still another aspect of the invention provides a system for creating a shunt between a first area and a second area having a lower pressure than the first area wherein the first and second areas are not connected prior to creating the shunt. The system may include a stent having a first end and a second end and a lumen extending between the first end and the second end. The system may further include a first anchoring feature at the first end and a second anchoring feature at the second end. The system may also include a delivery device for carrying the stent to an implantation site.

In at least one embodiment, the delivery device further includes a shaped balloon that, when expanded in said stent, forms a flange in said stent at at least one of the first and second ends.

The stent of the system may further include a flow control mechanism within the lumen.

The stent of the system may also include a self-expanding flange at at least one of the first and second ends.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 6b is a perspective view of the embodiment of FIG. 6a;

FIG. 14 is a is a perspective view of an embodiment of the invention;

FIG. 15 is a perspective view of an embodiment of the invention;

FIG. 16 is a perspective view of an embodiment of the invention in a closed or constricted configuration;

FIG. 17 is a perspective view of the embodiment of FIG. 16 in an expanded configuration;

FIG. 18 is a perspective view of an embodiment of the invention in a closed or constricted configuration;

FIG. 19 is a perspective view of the embodiment of FIG. 18 in an open configuration;

FIG. 64 is a diagram of a step of an embodiment of a method of the invention;

FIG. 65 is a diagram of a step of an embodiment of a method of the invention;

FIG. 66 is a diagram of a step of an embodiment of a method of the invention;

FIG. 67 is a diagram of a step of an embodiment of a method of the invention;

FIG. 68 is an elevation of an embodiment of a device of the invention;

FIG. 69 is an end view of the device of FIG. 68 in an expanded state;

FIG. 70 is a side elevation of the device of FIG. 68 in an expanded state;

FIG. 71 is an elevation of an embodiment of a device of the invention;

FIG. 72 is an end view of the device of FIG. 71 in an expanded state;

FIG. 73 is a side elevation of the device of FIG. 71 in an expanded state;

FIG. 83 is a perspective view of an embodiment of a device of the invention;

FIG. 84 is an elevation of an embodiment of a device of the invention;

FIG. 85 is a side elevation of the device of FIG. 84 in an expanded state;

FIG. 100 is a diagram showing a step of a method of the invention;

FIG. 101 is a diagram showing a step of a method of the invention;

FIG. 102 is a diagram showing a step of a method of the invention;

FIG. 103 is a diagram showing a step of a method of the invention; and,

FIG. 104 is a diagram showing a step of a method of the invention.

DESCRIPTION OF EMBODIMENTS

Figure 1:
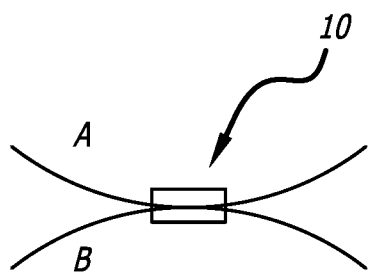
FIG. 1 is a diagram of a flush connection made according to an embodiment of a method of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The shunt devices of the invention generally include connection devices, lumens, anchoring features, and flow-control mechanisms.

Connection Devices

The devices of the present invention are generally connectors that join two or more bodily chambers or vessels, or a combination thereof, together and allow fluid or gas to flow between them. The connectors may be made of metal, polymers, a hybrid of each or in combination. It may have spring like properties that enable it to press against tissue walls holding them compressed together. It may be expansile, keeping tissue apart, and may be self-expanding or expandable such as by a balloon expandable technique. The surface of the connector may be textured to enhance compatibility, promoting cell inward cell growth or as a covering as described in more detail below.

Generally, the connection devices function to pull tissues together either flush with each other or within a specified and desired distance. The tissue is secured firmly to prevent leakage of fluid or gas external to the desired path. A tissue bond may also be created by pressure sealing and may form healthy scar tissue which invades the connection and functions as a strong adhesive via fibrosis over time. The device may facilitate a specific type of tissue such as fibrous tissue, endothelial tissue, epithelial tissue or any other tissue of the body, which functions both to seal and also to perform biologic functional activity.

Such functional activity may include rendering a device biocompatible or more biocompatible through a thin tissue interface what develops on the device. In this manner, the device grows tissue over itself for biocompatibility. Such compatibility may include blood (for example, preventing clots or thrombus), or biocompatibility that prevents inflammatory or immune responses from occurring due to the presence of the device. The surface of the device thus promotes biologic covering, but also may promote tissue growth within the device itself, completely or nearly completely surrounded by the device. A combination of these may be made by designing a mechanical structure that has interstices for both covering and also within the interstices which remain as porous but are covered with biologic materials which progresses over time to create a hybrid device-both mechanical and biologic. In this context a device becomes "living" since it has cells for viability but also mechanical structure for strength and for function.

The physical characteristics of the device vary based on the intended application and size of the patient. For example, in some instances, it may be desired for two bodily chambers or organs to be flush. In other instances, it may be desired for the two bodily chambers to be spaced apart.

FIG. 1 is a diagram showing a flush connection 10 between a bodily chamber A and a bodily chamber B.

Figure 2:
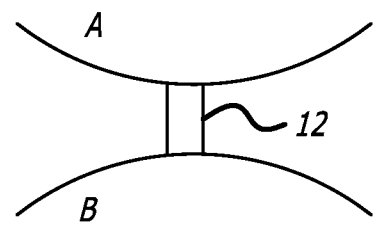
FIG. 2 is a diagram of a tubular, non-flush, or spaced apart connection made according to an embodiment of a method of the invention.

FIG. 2 is a diagram showing a non-flush or spaced apart connection, such as a tubular connection, 12 between a bodily chamber A and a bodily chamber B. The purpose of a longer connector such as a leak-proof tube will be useful for connecting organs which may not be opposed to one another. This embodiment may be useful, for example, if the left internal mammary artery is desired to be connected to a coronary artery which is diseased. In this case a connection could be made using a small tube functioning as a transit for blood.

It should also be noted that the connectors described herein can be used to create flush connections between organs that are not naturally in contact with each other. Similarly, the connector described herein can be used to create non-flush connections between organs that are naturally in contact with each other. In other words, the anchoring properties of the connectors are sufficient to be able to manipulate bodily chambers and vessels and hold them in a desired location, relative to other bodily chambers and/or vessels.

Figure 3:
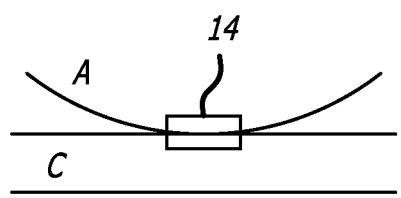
FIG. 3 is a diagram of a chamber-to-vessel connection made according to an embodiment of a method of the invention.
Figure 4:
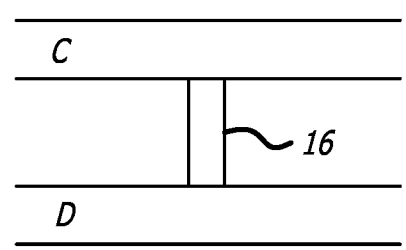
FIG. 4 is a diagram of a vessel-to-vessel connection made according to an embodiment of a method of the invention.
Figure 5:
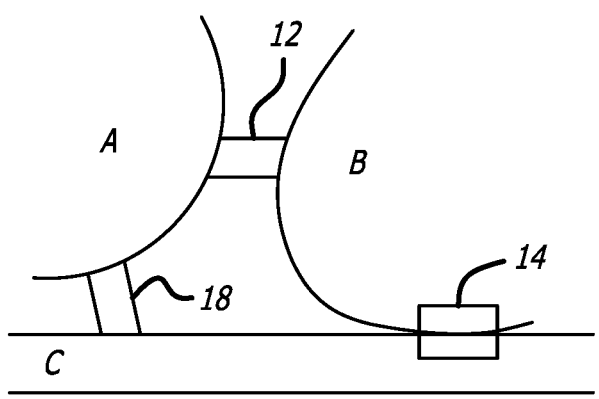
FIG. 5 is a diagram of a multiple connection made according to an embodiment of a method of the invention.

FIGS. 1 and 2, described above, show two bodily chambers being connected. In some instances, it may be desired to connect a bodily chamber to a vessel, a vessel to a vessel, or make multiple connections therebetween. By way of example only, FIG. 3 shows a flush connection 14 between a bodily chamber A and a vessel C. FIG. 4 shows a non-flush connection 16 between a vessel C and a vessel D. FIG. 5 shows a non-flush connection 12 between bodily chambers A and B, combined with a flush connection 14 between bodily chamber B and vessel C, and a non-flush connection 18 between bodily chamber A and vessel C.

Figure 6A:
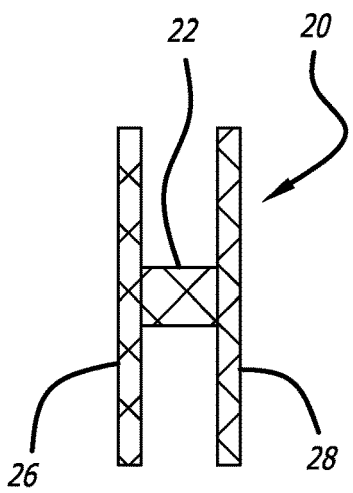
FIG. 6a is a side elevation of an embodiment of a device of the invention.
Figure 6B:
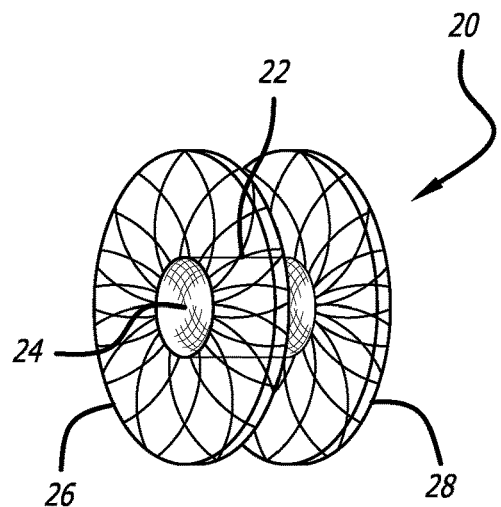

FIGS. 6a and 6b show a simple embodiment 20 of a device of the invention. The device 20 is a shunt that has a body 22 defining a lumen or anastomosis 24 therethrough and anchoring features 26 and 28 on either side of the device 20. The device 20 is representative of a shunt used to make a flush connection as the anchoring features 26 and 28 do not grip on both sides of a single chamber wall. Rather, anchor 26 grips on the interior wall of a first bodily chamber or vessel and anchor 28 grips on an interior wall of a second bodily chamber or vessel. By way of example, device 20 is shown as a braided device. However, the device 20 could be similarly fenestrated, such as laser-cut from a tube, or the device 20 could be woven, solid, mesh, etc.

Figure 88:
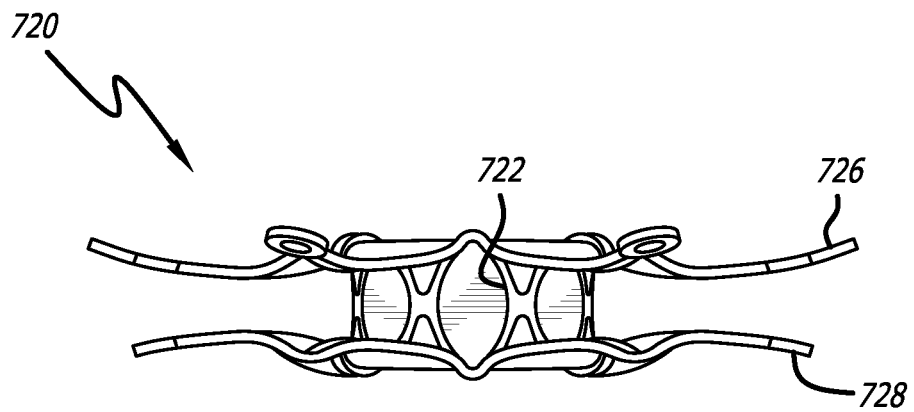
FIG. 88 is a side elevation of an embodiment of a device of the invention.
Figure 89:
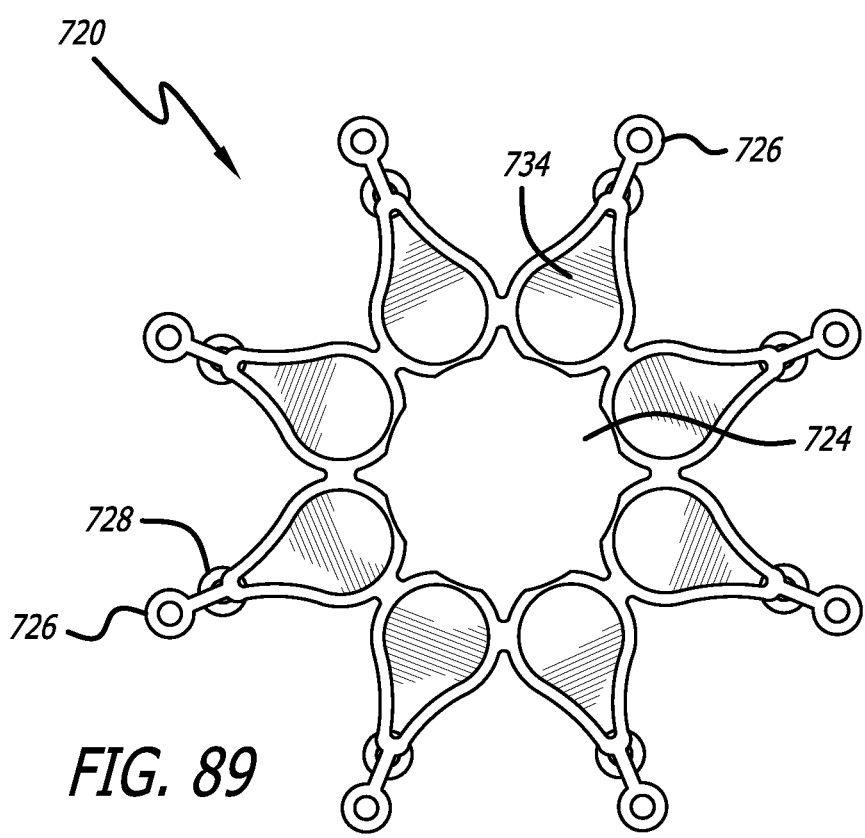
FIG. 89 is a top plan view of an embodiment of a device of the invention.
Figure 90:
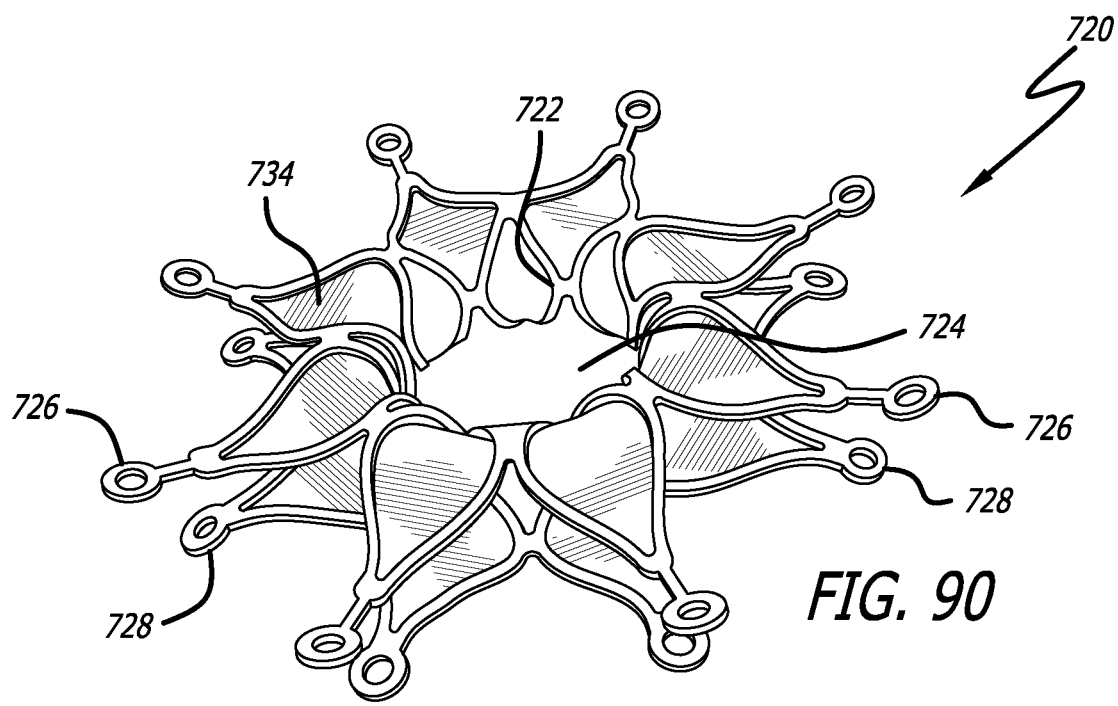
FIG. 90 is a perspective view of an embodiment of a device of the invention.

For example, FIGS. 88-90 show a specific embodiment 720 of a device having a fenestrated body 722 that is laser cut from a tube. Device 720 is a shunt that has a body 722 defining a lumen or anastomosis 724 therethrough and anchoring features 726 and 728 on either side of the device 720. The device 720 makes a flush connection as the anchoring features 726 and 728 do not grip on both sides of a single chamber wall. Rather, anchor 726 grips on the interior wall of a first bodily chamber or vessel and anchor 728 grips on an interior wall of a second bodily chamber or vessel.

Anchoring features 726 and 728 are embodied as a plurality of petals. The embodiment of FIGS. 88-90 show anchoring features 726 and 728 that include eight petals each. The petals 730 and 732 do not have to be identical to each other. For example, in FIGS. 88-90, the petals 730 are radially longer than the petals 732. The specific designs are tailored to the implantation site and the application of the shunt.

By way of example, the device 720 of FIGS. 88-90 has a body 720 that has a length of about 2.25 mm, an OD of approximately 4.25 mm and an ID of about 4 mm. The petals 730 and 732, when expanded, are separated by approximately 1 mm to 1.25 mm. The diameter of the upper petals 730 is about 13 mm and the diameter of the lower petals 732 is about 11.5 mm.

The device 720 is shown with a cover 734 spanning between the various features of the device 720. The cover 734 aids in anchoring the device 720 and preventing leakage of fluids around the device. The cover 734 may further promote ingrowth.

Figure 91:
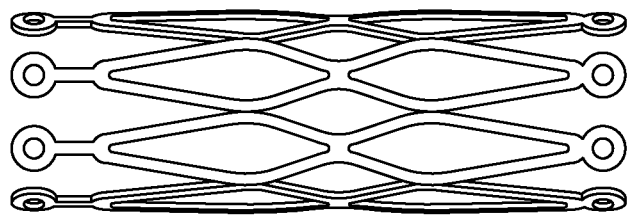
FIG. 91 is a side elevation of an embodiment of a device of the invention.
Figure 92:
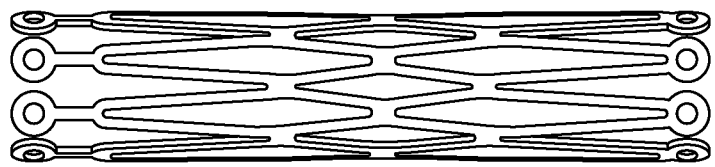
FIG. 92 is a side elevation of an embodiment of a device of the invention.
Figure 93:
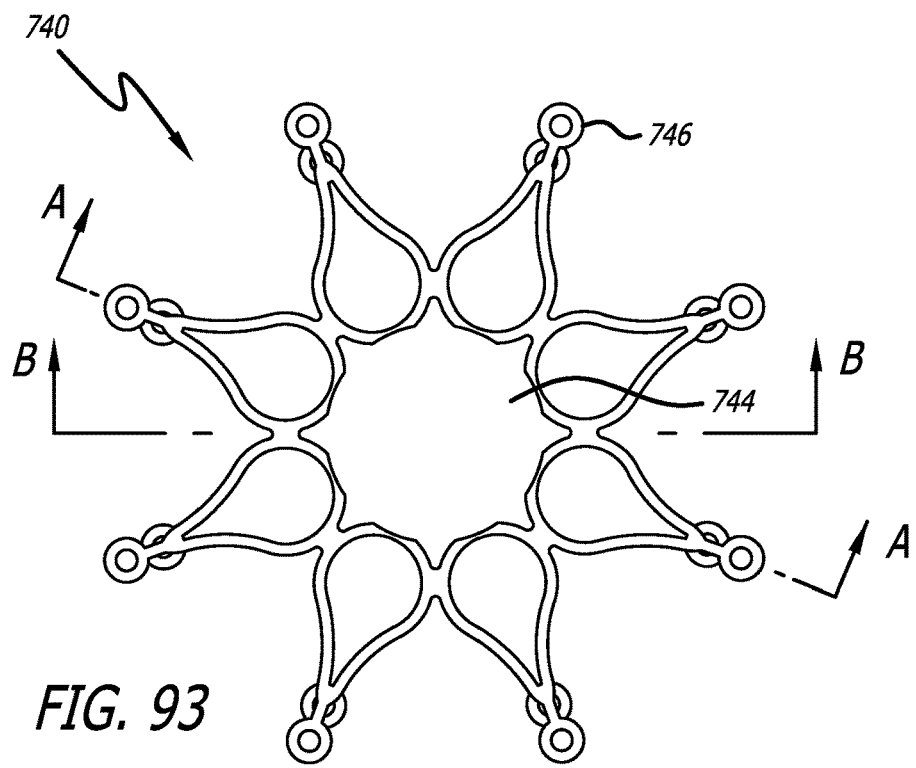
FIG. 93 is a top plan view of an embodiment of a device of the invention.

FIGS. 91 and 92 show the device 720, without the cover 734, and in the form of a tube. FIG. 92 shows the device 720 in a compressed configuration and FIG. 93 shows the device in a first expanded configuration. Further expansion would result in the second expanded configuration shown in FIGS. 88-90. In some embodiments, the device shown in FIG. 91 would be a resting state having approximately the same dimensions as the tube from which the device 720 was cut. The configuration of FIG. 92 is then a compressed configuration and the device would expand to the configuration of FIG. 91 when released. The device would then be further expanded to the second expanded configuration of FIGS. 88-90, such as with a balloon or via thermal expansion if memory metals are used.

In other embodiments, FIG. 92 shows the resting state of device 720, having approximately the same diameter as the tube from which it was cut. The configuration of FIG. 91 is then the result of a first expansion, either thermally or mechanically, and the configuration is the result of a second expansion, either thermally or mechanically.

Figure 94:
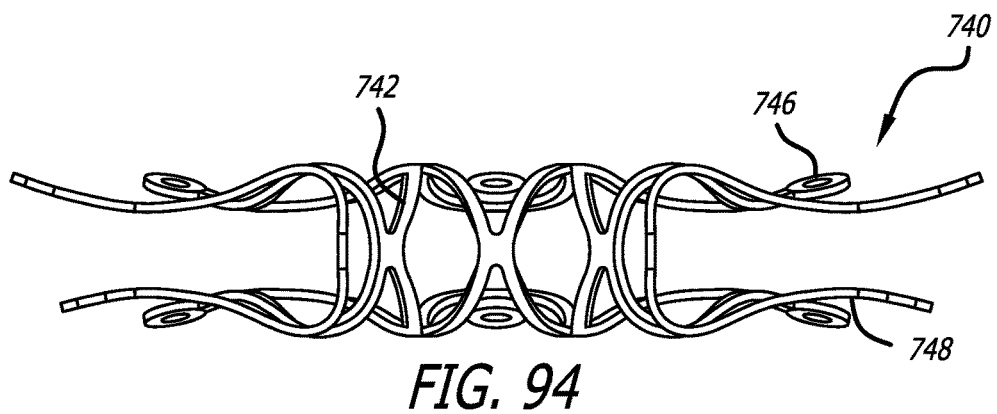
FIG. 94 is a section view taken along section lines A-A of FIG. 93.
Figure 95:
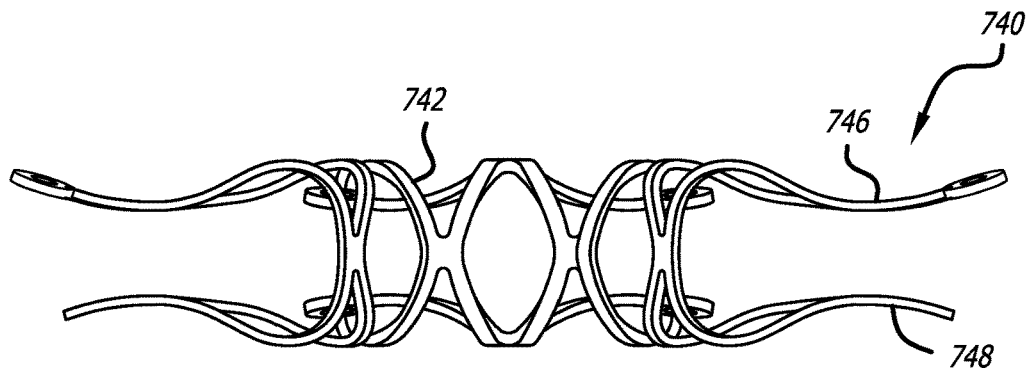
FIG. 95 is a section view taken along section lines B-B of FIG. 93.

FIGS. 93-95 show an embodiment 740 of a device that is similar to embodiment 720, but remains uncovered. The device 740 has a fenestrated body 742 that is laser cut from a tube. Device 740 is a shunt that has a body 742 defining a lumen or anastomosis 744 therethrough and anchoring features 746 and 748 on either side of the device 740. The device 740 makes a flush connection as the anchoring features 746 and 748 do not grip on both sides of a single chamber wall. Rather, anchor 746 grips on the interior wall of a first bodily chamber or vessel and anchor 748 grips on an interior wall of a second bodily chamber or vessel.

Anchoring features 746 and 748 each include a plurality of petals 750 and 752, respectively. The embodiment of FIGS. 93-95 show anchoring features 746 and 748 that include eight petals each. The petals 750 and 752 do not have to be identical to each other. For example, in FIGS. 93-95, the petals 750 are radially longer than the petals 752. The specific designs are tailored to the implantation site and the application of the shunt.

By way of example, the device 740 of FIGS. 93-95 has a body 740 that has a length of about 2 mm, an OD of approximately 5.4 mm (measured to the intersection of the petals 750) and an ID of about 4 mm. The petals 750 and 752, when expanded, are separated by approximately 1 mm to 1.25 mm. The diameter of the upper petals 750 is about 13 mm and the diameter of the lower petals 752 is about 11.5 mm.

Figure 96:
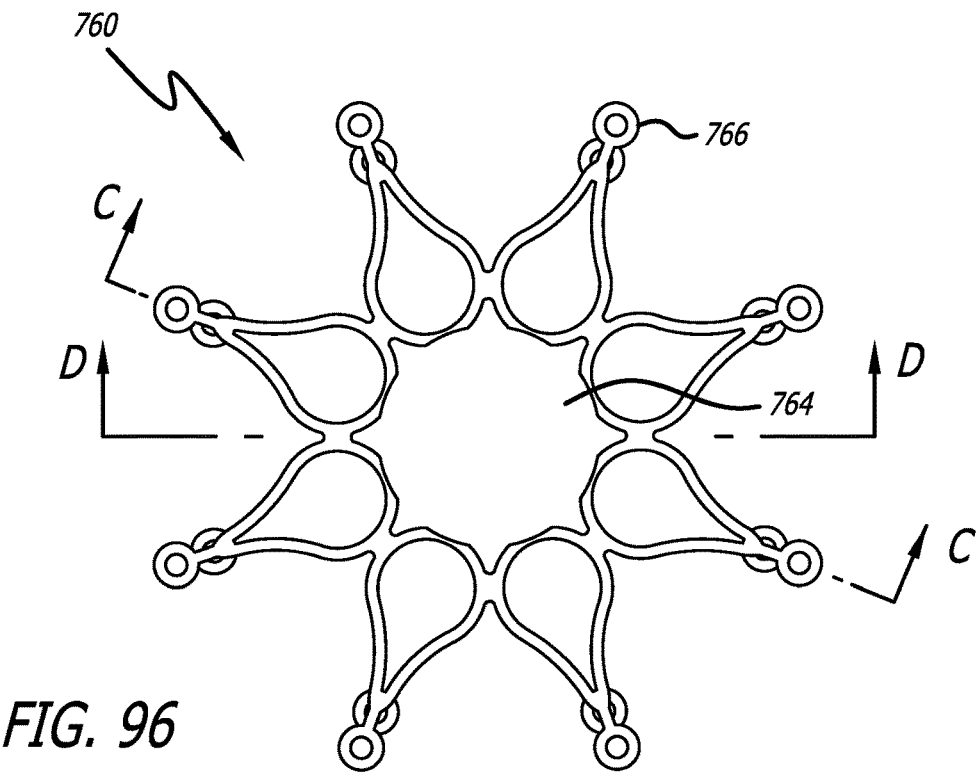
FIG. 96 is a top plan view of an embodiment of a device of the invention.
Figure 97:
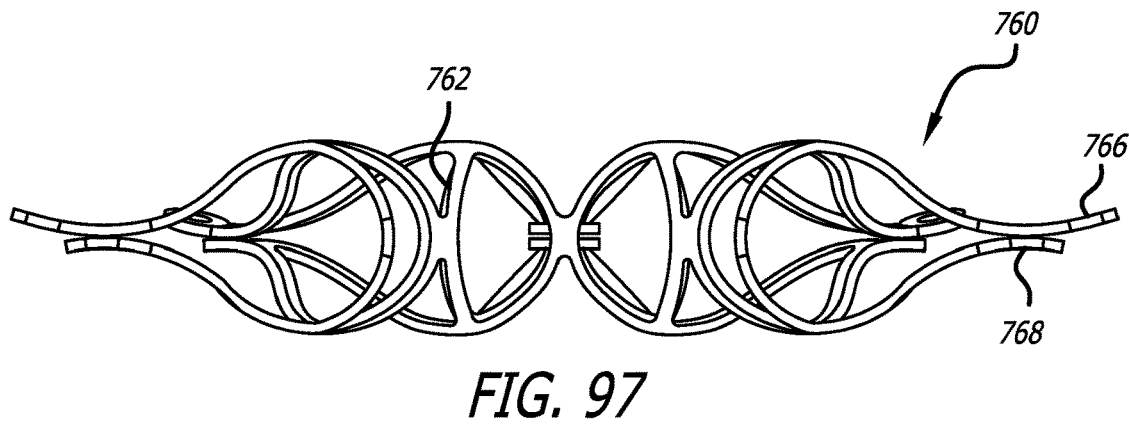
FIG. 97 is a section view taken along section lines A-A of FIG. 96.
Figure 98:
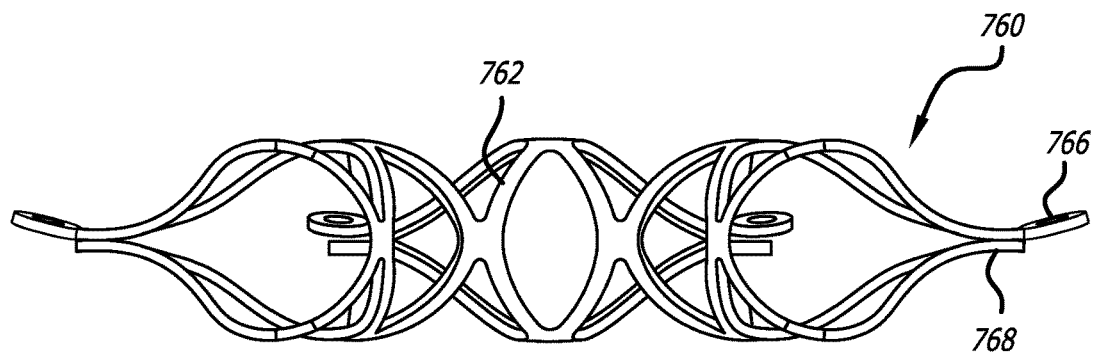
FIG. 98 is a section view taken along section lines B-B of FIG. 96.

FIGS. 96-98 show an embodiment 760 of a device that is similar to embodiment 740. The device 760 has a fenestrated body 762 that is laser cut from a tube. Device 760 is a shunt that has a body 762 defining a lumen or anastomosis 764 therethrough and anchoring features 766 and 768 on either side of the device 760. The device 760 makes a flush connection as the anchoring features 766 and 768 do not grip on both sides of a single chamber wall. Rather, anchor 766 grips on the interior wall of a first bodily chamber or vessel and anchor 768 grips on an interior wall of a second bodily chamber or vessel.

Anchoring features 766 and 768 each include a plurality of petals 770 and 772, respectively. The embodiment of FIGS. 96-98 show anchoring features 766 and 768 that include eight petals each. The petals 770 and 772 do not have to be identical to each other. For example, in FIGS. 96-98, the petals 770 are radially longer than the petals 772. The specific designs are tailored to the implantation site and the application of the shunt.

By way of example, the device 760 of FIGS. 96-98 has a body 760 that has a length of about 2 mm, an OD of approximately 5.7 mm (measured to the intersection of the petals 750) and an ID of about 4 mm. The petals 770 and 772, when expanded, are curl from a maximum separation of 2 mm toward each other so they are touching or nearly touching each other. In this way, the have a greater clamping force than the embodiment 740. The diameter of the upper petals 750 is about 13 mm and the diameter of the lower petals 752 is about 11.6 mm.

Figure 7:
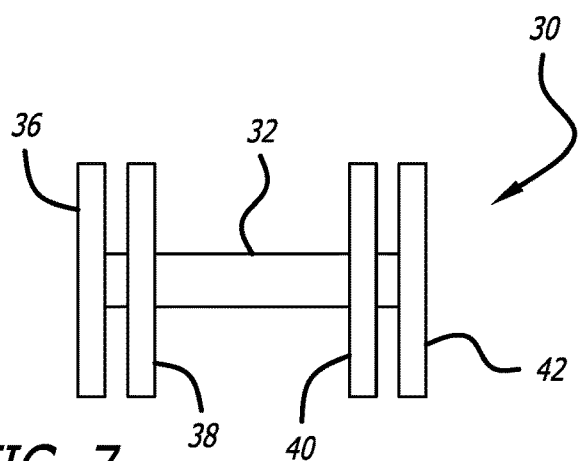
FIG. 7 is a side elevation of an embodiment of a device of the invention.
Figure 8:
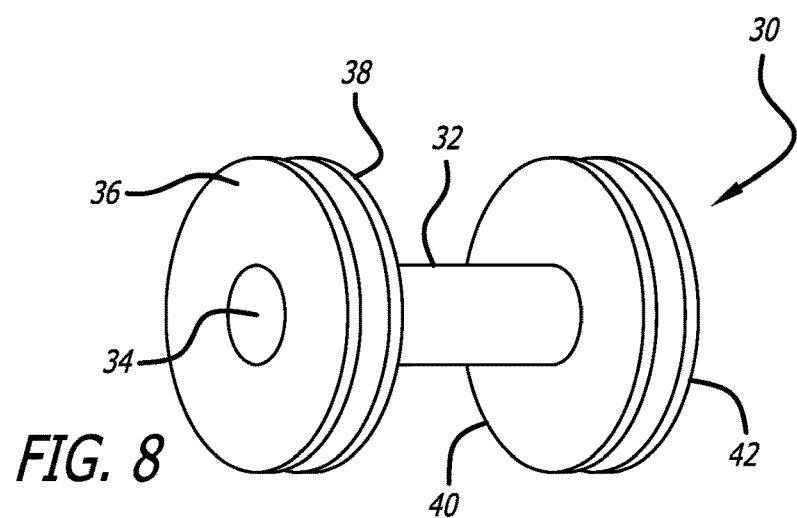
FIG. 8 is a perspective view of the embodiment of FIG. 7.

If it is desired to maintain spacing between the chambers or vessels, a non-flush connector or shunt device is used. FIGS. 7 and 8 provide a simple embodiment 30 of a non-flush connector or shunt device. The device 30 includes a body 32 defining a lumen 34 therethrough. The anchor features include a first anchor 36 for placement on an inside wall of a first bodily chamber or vessel, a second anchor 38 for placement on an outside wall of the first bodily chamber opposite the first anchor 36, such that the first bodily chamber or vessel wall is sandwiched therebetween. There are also third and fourth anchors 40 and 42 for similar positioning outside and inside of a second bodily chamber or vessel, respectively.

The anchor features may be mechanical in nature, such as the flanges shown in FIGS. 5-8, or they can involve coatings that promote ingrowth, adhesives, surface textures, barbs, hooks, clamps, screws, Nitinol folds, levers, flares, expandable cloths, clips, wires, balloons and the like, just to name a few. Or they may be a combination of one or more of these examples or other, unlisted embodiments. Additionally, the anchor features may have elastic or spring-like properties such that the anchor features exert a force on the engaged tissues such that migration is unlikely. The anchor features themselves may exert the spring force on the tissue by virtue of the materials used, such as would be the case with memory metals like Nitinol, or the spring like properties exerted by the anchor features may be the result of an elastic body stretched between the two bodily chambers or vessels. Thus, when the elastic body is stretched and is biased toward an original, shortened length, the anchor features are pulled toward each other, thus clamping the tissue between the anchor features.

Figure 9:
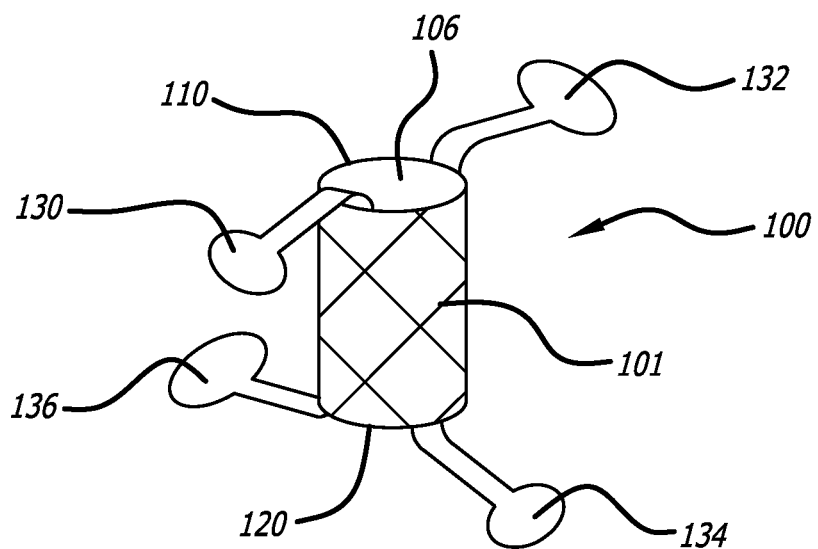
FIG. 9 is a perspective view of an embodiment of the invention.

FIG. 9 shows another embodiment of a connector or shunt 100 of the invention. Shunt 100 includes a braided tubular body 101 having a first end 110 and a second end 120. The tubular body 101 defines a lumen 106 that passes through the body 101 and is used for the transference of bodily fluids or gasses.

An anchoring mechanism is provided at the first end and the second end of the shunt to anchor itself within each of the connecting chambers and/or vessels and can be provided with various means to anchor it in position, such as expandable cloths, hooks, barbs, flanges, clips, wires, flares, balloons and the like.

The anchoring mechanism of FIG. 9 is in the form of single-arm flanges 130, 132, 134 and 136. In the embodiment shown, flanges 130 and 132 radiate from the first end 110 and flanges 134 and 136 radiate from the second end 120. These arms are used to anchor the shunt lumen 100 within each of the connecting chambers and/or vessels. These arms may be heat-set memory metals so that the self-expand or spread after being released from a delivery sheath. Or they may be malleable and positioned manually during the delivery procedure.

Figure 10:
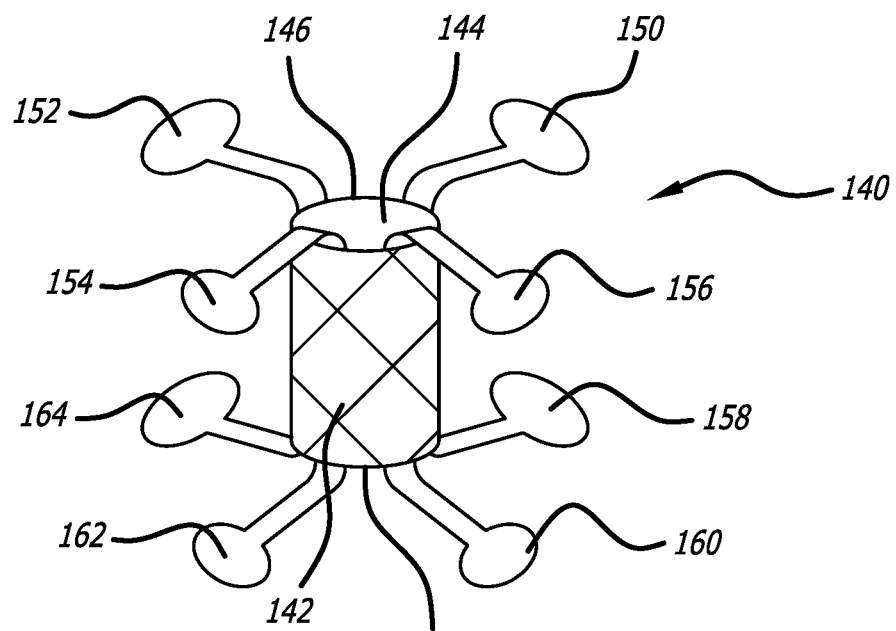
FIG. 10 is a perspective view of an embodiment of the invention.

FIG. 10 shows an embodiment of a shunt 140 having a body 142 defining a lumen 144 that extends from a first end 146 of the body 142 to a second end 148 of the body 142. The shunt 140 includes as anchoring features, four arms 150, 152, 154 and 156 radiating from the first end 146 and four arms 158, 160, 162 and 164 extending from the second end 148. These arms may be heat-set memory metals so that the self-expand or spread after being released from a delivery sheath. Or they may be malleable and positioned manually during the delivery procedure.

FIGS. 68-87 show additional stent designs. FIGS. 68-70 depict a stent 500 that minimizes the amount of implanted material. The stent 500 allows for anchoring and includes cloth 502 that forms a shunt orifice 504 and applies the radial force to open the native tissue. The radial force also serves to anchor the stent 500. The cloth 502 is attached to the frame 500 such that when the frame reaches its final shape, the cloth 502 is taught enough to push the native tissue out of the way. FIG. 68 shows the stent 500 as cut during manufacturing. FIG. 69 is a top view of the stent 500 in a deployed state. FIG. 70 is a side elevation of the stent 500 in a deployed state.

FIGS. 71-73 depict a stent 510 that also minimizes the amount of implanted material. The stent 510 is similar to the stent 500 but includes arms. The stent 510 allows for anchoring and includes cloth 512 that forms a shunt orifice 514 and applies the radial force to open the native tissue. The cloth 512 is attached to the frame 510 such that when the frame reaches its final shape, the cloth 512 is taught enough to push the native tissue out of the way. The arms 516 extend from the stent frame, and may be integral therewith, and attach to the cloth to provide additional force. FIG. 68 shows the stent 510 as cut during manufacturing. FIG. 69 is a top view of the stent 510 in a deployed state. FIG. 70 is a side elevation of the stent 510 in a deployed state.

Figure 74:
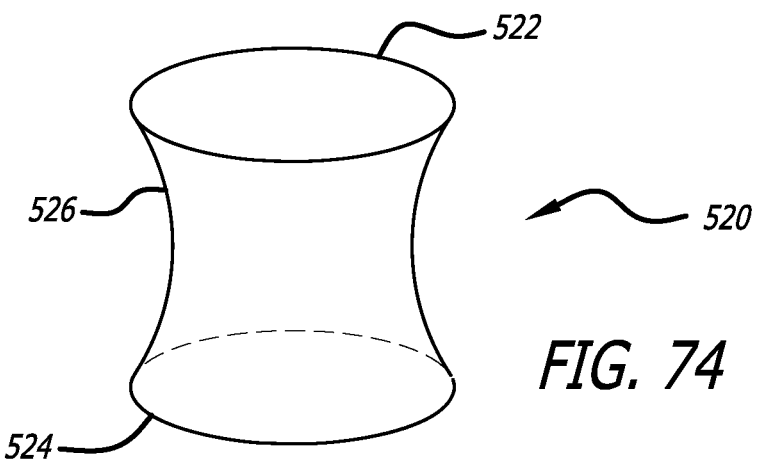
FIG. 74 is a perspective view of an embodiment of a device of the invention.

FIG. 74 depicts a shunt 520 that employs attachment members that comprise simple nitinol or shape memory wire rings 522 and 524 that are bridged with a piece of cloth 526 that is attached to the rings such that the desired shunt size is formed when the rings are fully deployed.

Figure 75:
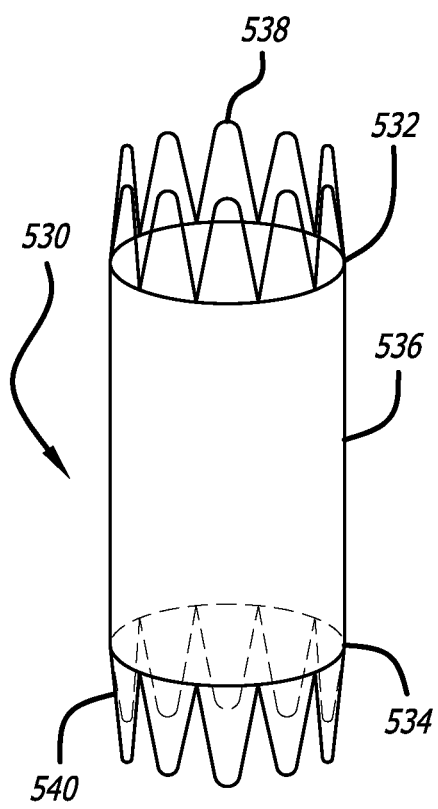
FIG. 75 is a perspective view of an embodiment of a device of the invention.
Figure 76:
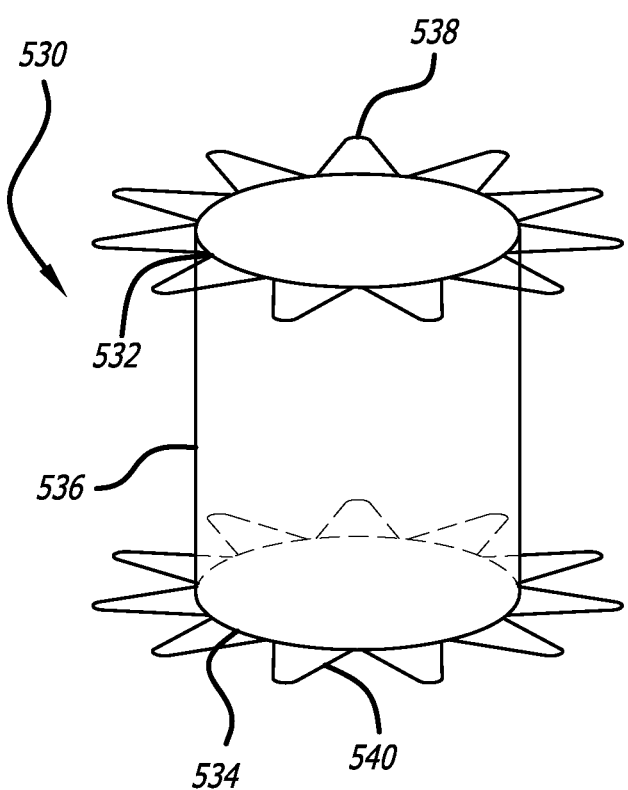
FIG. 76 is a perspective view of an embodiment of a device of the invention.

FIG. 75-76 is a shunt design 530 that is similar to shunt or stent 520 except it further includes anchoring flanges 538 and 540 extending from the rings 532 and 534. FIG. 75 shows the device 530 in a predeployed state with flange 538 extending upward from the first ring 532 and flange 540 extending downward from the second ring 534. Rings 532 and 534 are joined by cloth 536. FIG. 76 shows the device 530 in a deployed state with flanges 538 and 540 extending radially or outwardly from the rings 532 and 534, respectively.

Figure 77:
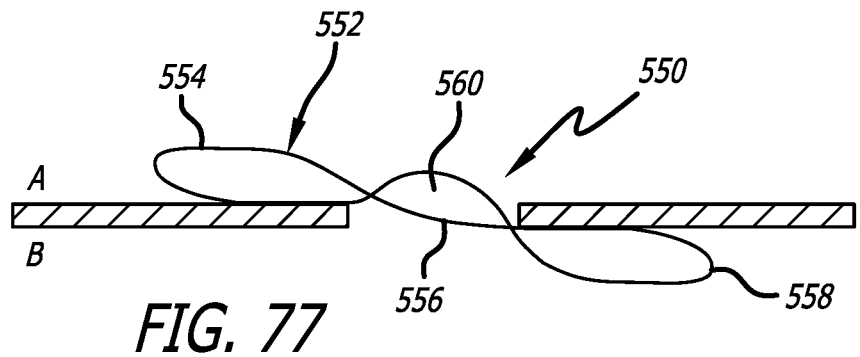
FIG. 77 is a side elevation of an embodiment of a device of the invention.

FIG. 77 shows a clip device 550. The clip device 550 is a minimal device that includes a wire 552 formed into three loops 554, 556 and 558. The center loop 556 forms a lumen 560 while the outer loops 554 and 558 are anchoring members. The embodiment 550 has the anchor members directly opposite each other. The anchor loops are large enough to secure the device between bodily chamber or vessel A and bodily chamber or vessel B.

Figure 78:
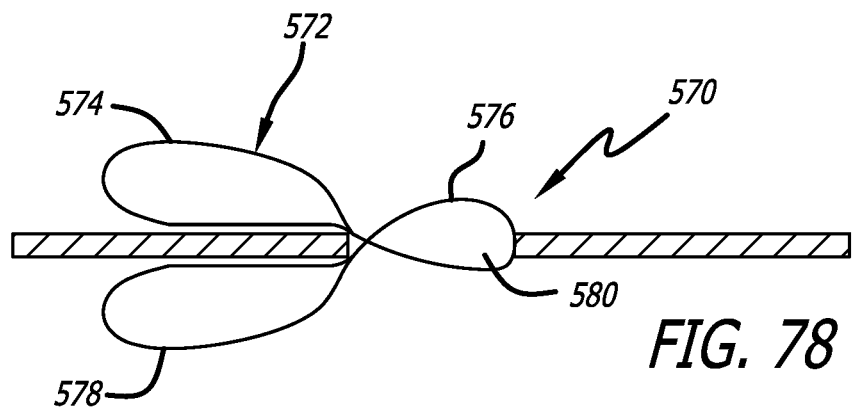
FIG. 78 is a side elevation of an embodiment of a device of the invention.

In some applications, the clip may be shaped differently. For example, FIG. 78 shows a similar clip device 570. The clip device 570 is a minimal device that includes a wire 572 formed into three loops 574, 576 and 578. The center loop 576 forms a lumen 580 while the other loops 574 and 578 are anchoring members. The embodiment 570 has the anchor members on the same side of loop 576 such that they may oppose each other on opposite sides of a chamber vessel wall or walls.

Figure 79:
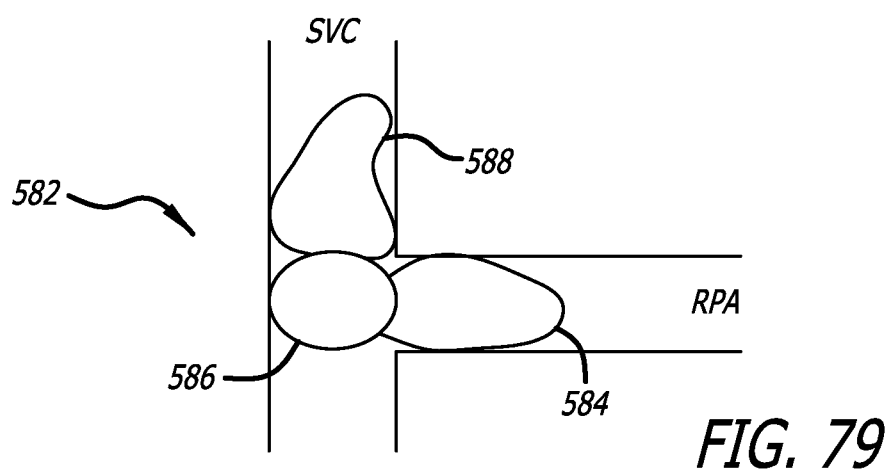
FIG. 79 is an end view of an embodiment of a device of the invention.

Similarly, FIG. 79 shows a top plan view of a clip 582 having three loops 584, 586 and 588. The loop 586 forms a lumen 590 and the loops 584 and 588 are separated from each other radially by 90 degrees or so. This embodiment may be useful when joining two vessels that are somewhat perpendicular to each other, such as the SVC and the RPA.

Figure 80:
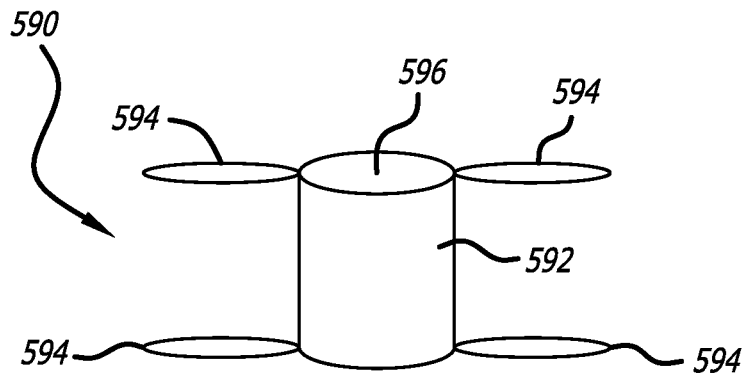
FIG. 80 is a perspective view of an embodiment of a device of the invention.

FIG. 80 shows an embodiment 590 of an RPA to SVC shunt. This shunt has an ID of about 4 mm. In this case a solid tube body 592 may be desirable as it is small enough that it is still deliverable from a 15 Fr catheter without having to compress the tube 592. A solid metallic or polymeric shunt body 592 would reduce the risk of device fatigue and blood stasis. This embodiment also eliminates the need for a stent covering. The device 590 is shown as including anchoring arms 594 but any of the anchoring mechanisms described herein could be used. The tube 592 defines a lumen 596.

Figure 81:
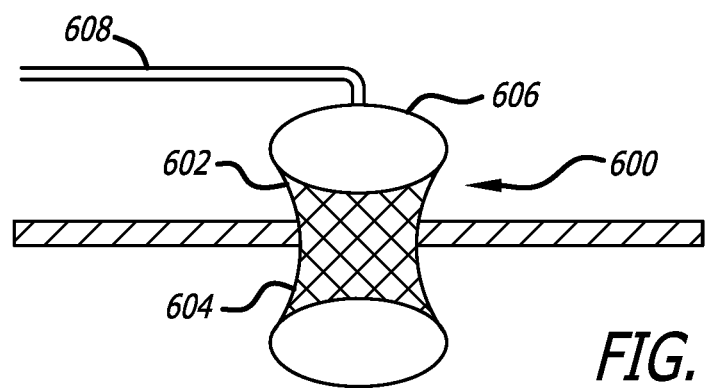
FIG. 81 is a side elevation of an embodiment of a device of the invention.

FIG. 81 shows an embodiment 600 of a balloon expandable stent. Rather than using a shape memory structure such as nitinol, a balloon expandable stent 600 could be deployed with an hourglass-shaped balloon 606, or just a balloon with a diameter that is equal to or greater than the final expanded flange diameter, and an inflation catheter 608 in order to create flanges 602 and 604 on either side of the tissue to produce adequate fixation force.

Figure 82:
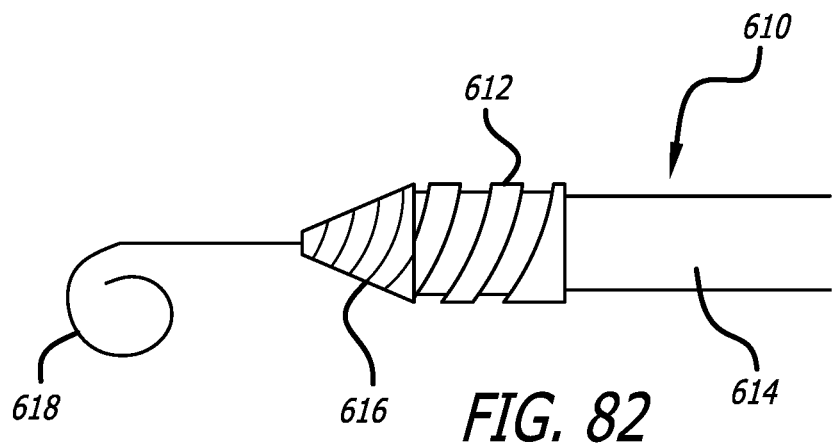
FIG. 82 is a side elevation of an embodiment of a device of the invention.

FIG. 82 shows a threaded shunt assembly 610. The assembly includes a threaded shunt 612 carried by a delivery device 614 that includes a threaded dilator 616 that is able to follow a guidewire 618. The shunt size, like that of device 590, is small enough to allow a solid tube to be used that has external threads that are used as an anchoring device. The threaded dilator drives the device into a lumen or chamber wall and can then be removed, leaving the threaded shunt 612 in place.

FIG. 83 shows a minimalist shunt 620 used to connect two vessels, such as the SVC and the PA, that are perpendicular to each other. The device 620 includes a tube 622 with a first anchoring ring 624 and a second anchoring ring 626. The rings are on opposite sides of the tube 622 but they are oriented perpendicularly to each other to match the orientation of the vessels. Multiple loops could be used on each end to increase purchase or attachment stability. Additionally, the wire loops could have geometric features that allow for a dampening or conformability element to them.

One limitation to traditional interventional shunts or closure devices is their inability to form a smooth transition between the adjacent anatomy and the device. This transition zone has the potential to cause stasis, which can lead to the formation of clots or thrombus. It was found that by over-inflating a covered stent graft with a larger balloon, the graft would dramatically foreshorten, and the ends would flare. This occurs because of the following mechanisms: (1) When the graft covering reaches full diameter it cannot increase in size and the length is at is longest length. (2) As a result, the larger inflation balloon takes an hourglass shape around the stent graft. (3) As the balloon is further inflated the larger ends of the balloon begin to collapse the stent in a linear manner with the ID being preserved because of the balloon. (4) The ends of the graft being to flare as the maximum pressure is reached.

These mechanisms can be applied in any stent graft to reduce its length, if desired. Additionally, stent embodiments are provided herein that take advantage of these mechanisms.

FIGS. 84 and 85 show a stent 630 that is covered with a material 632 that is foldable, however, once its final diameter is reached it does not increase further in diameter, regardless of increased balloon pressure. The stent geometry is such that it can be radially and linearly collapsed. Stent 630 includes independent stent structures 634 that are only connected via the covering material. Alternatively, the radial stent features 634 could be attached via intermittent or minimalistic features 636 such that the resistance to linear displacement is minimal.

The ends of the stent 630 include end flanges 638 and 640 to aid in fixation, flow dynamics and the transition with the surrounding tissue to minimize stasis; the end portions of the stent could be uncovered or the covering material could be elastic or attached in a way that would allow for further radial expansion compared to the main body of the implant.

One aspect of the invention involves interprocedurally adjustable shunts. The desired size of a shunt can vary from patient to patient. Pre-op workups can be helpful to estimate the size of the desired shunt size that is optimal for each patient, however, hemodynamic conditions can be unpredictable, and the shunt size may need to be adjusted during the procedure for optimal results.

Some methods of the present invention to achieve intraprocedural adjustability include, but are not limited to:

Providing a suture around the main body of a shunt that can be loosened or tightened then locked at the desired diameter; utilizing a braided structure that increases or decreases in diameter depending on its length and then locked in place; providing a shunt that has an internal cloth member that creates the effective shunt orifice. This cloth member can be twisted such that it forms an iris shape and then locked at the desired size; providing an outer structure that has a funnel shape with an internal structure that has a wedge shape. As the wedge is moved in or out of the funnel shape the effective orifice increases or decreases in size and then locked; providing a balloon expandable shunt that is deployed at a small ID and can be incrementally expanded to larger ID by increasing balloon pressure.

Figure 86:
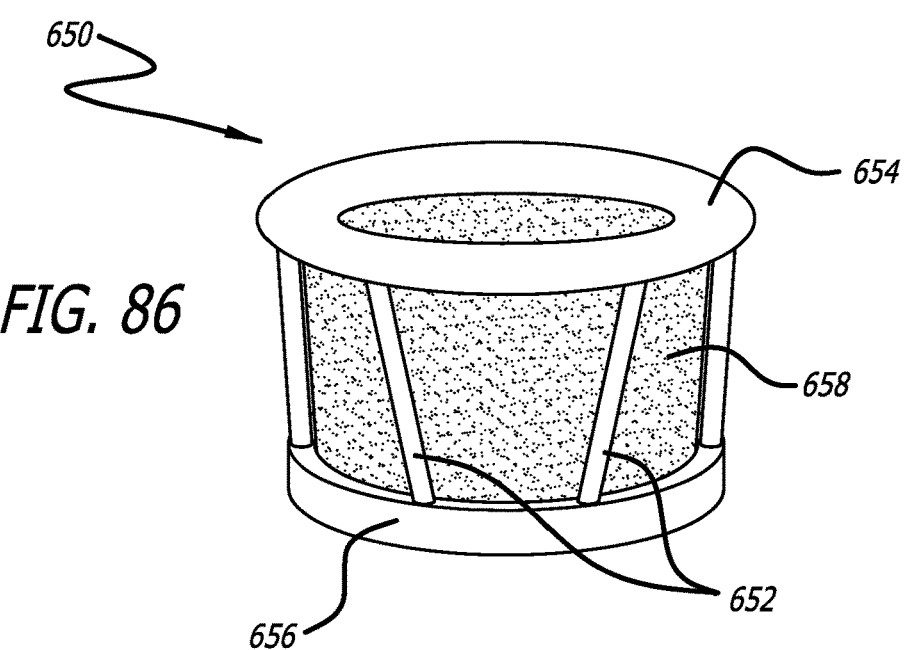
FIG. 86 is a photograph of an embodiment of a device of the invention.

FIG. 86 is a photograph of a fully polymeric balloon shunt 650 of the invention. The shunt 650 is uses multiple tubular balloons 652 as vertical struts that support two end ring-shaped balloons 654 and 656. The balloon(s) can be filled with two part epoxy or a UV cure solution to solidify and hold the shape chronically. The series of balloons could be covered with a lining 658 made of cloth, polymer, tissue, etc. for hemostasis.

Figure 87:
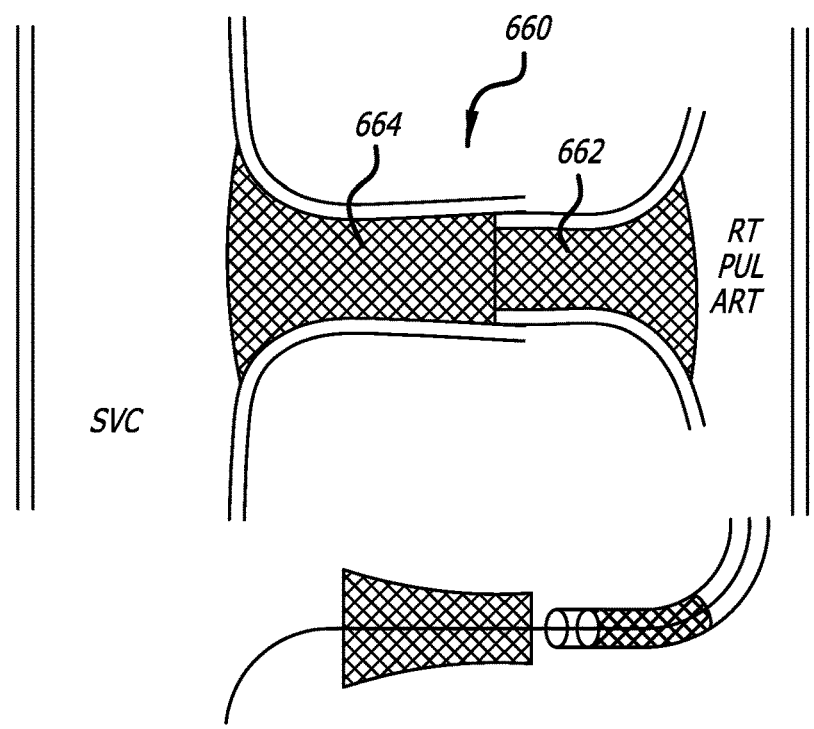
FIG. 87 is a side elevation of an embodiment of a device of the invention

FIG. 87 shows a shunt 660 that has an adjustable length. The shunt 660 includes a first stent 662 that can be deployed inside a second stent 664 to extend the total length of the shunt 660.

Lumens

The lumen allows fluid or gas to flow through the device. The lumen may control the amount of fluid, and/or the flow rate of the fluid, by virtue of the size and/or shape of the lumen.

Figure 11:
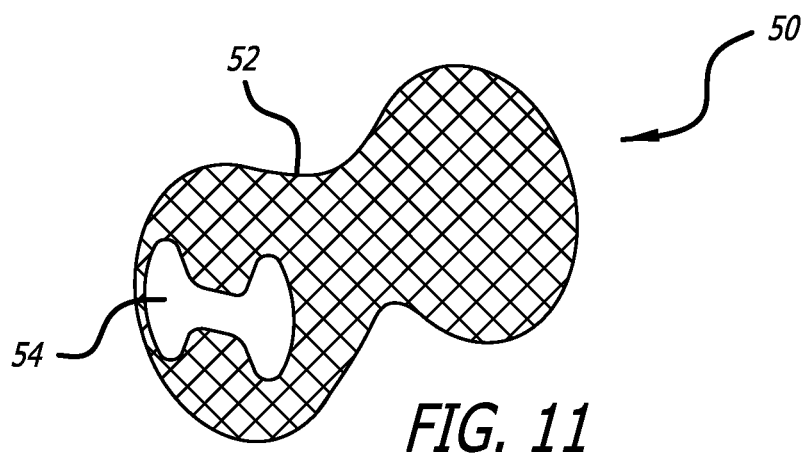
FIG. 11 is a perspective view of an embodiment of the invention.
Figure 12:
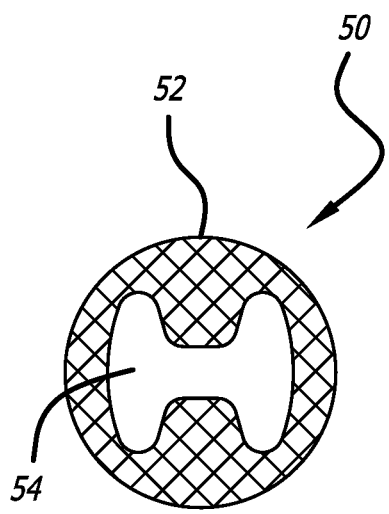
FIG. 12 is an end view of the device of FIG. 11.
Figure 13:
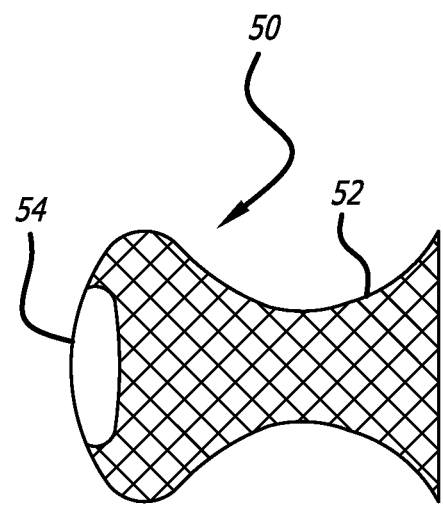
FIG. 13 is a side elevation of the device of FIG. 11.

The connection orifice leading to the lumen may be circular, elliptical or any other shape which promotes efficient and safe flow of blood or other fluids or gasses. One embodiment of a shaped lumen is shown in FIGS. 11-13. The shunt 50 includes a body 52 that defines a lumen 54 with an "H" shape, useful for controlling flow from an aorta to the superior vena cava. The "H" shape expands when subjected to increased pressures and may be ideally adapted for treating pulmonary hypertension. The expansive nature of this device makes it an adaptive shunt, which is explained in more detail below.

Additionally, the lumen may be divided by arms or similar features in order to reduce the flow rate and thus reduce the risk of hemolysis.

The lumen may further incorporate a screen or filter which prevents objects (such as clots) from migrating from one chamber to another.

One application of a filtered connection would be connection between a left heart and right heart structure such as the left atrium (left heart structure) and a pulmonary artery (right heart structure). Using a filtered connection would prevent particulates from flowing through the pulmonary vein and the pulmonary artery R-L shunt. This connection would require a macroscopic or large-hole filter to prevent systemic emboli traveling from the right heart to the body structures such as the brain. Pores in such a filter might be on the order of 100 microns to 1.5 mm size.

Some applications would benefit from a cellular filter that prevents cells from leaving one chamber into another. Pores in such a filter might be on the order of 10 microns or less. Yet another device selectively allows proteins or other biochemicals to either move or be prevented across the connection. The filter may be used to selectively prevent or facilitate materials from moving from one chamber to the other, keeping materials either within or keeping them out of a chamber or vessel.

FIG. 14 shows an example of a macroscopic filter 56 that could be used over the entrance of a shunt of the invention or could be placed within the entrance of a shunt or throughout the entire lumen of the shunt of the invention. The filter 56 is drawn as a screen, indicating the macroscopic, high-flow, low-resistance nature of the filter. One skilled in the art will realize other designs such as a woven or unwoven fibers, porous materials, fabrics, just to name a few, could be used in this application.

FIG. 15 shown an example of a cellular or microscopic filter 58 that may be used to selectively prevent materials from migrating through the shunt. This filter 58 could be used over the entrance of the shunt or placed within the entrance or throughout the entire lumen of the shunt. This filter 58 is drawn as a porous material to differentiate it from FIG. 14 but one skilled in the art will realize other materials such as a woven or unwoven fibers, porous materials, fabrics, just to name a few, could be used in this application.

Flow Control Mechanisms—Adaptive or Pressure-Driven Shunt Designs

As introduced above, the lumen through the shunt allows fluid or gas to flow through the device and can be used to control the fluid dynamics of the flow through the device. The device may further incorporate a flow control device that allows flow through the lumen on only one direction, allows flow through the lumen in only one direction and only if certain parameters are met. Alternatively, the device may further incorporate a flow control device that allows flow through the lumen in both directions, but only when certain parameters are met. The parameters that must be met in a first direction for fluid flow to be established may be the same or different than the parameters that must be met for fluid to flow in a second direction.

Adaptive shunt designs vary the flow profile based upon the pressure drop across the device. The principal of an adaptive shunt is such that the degree of shunting conferred by the device can be changed by intrinsic local conditions in response to a change in hemodynamic and/or anatomic parameters around which the device is placed. Such parameters may include, but are not limited to pressure, pressure gradient, absolute flow or flow gradients. The relationship between shunting and stimulus-response can be linear or nonlinear depending on the requirements of the individual situation. In addition to linearity/nonlinearity, thresholds can be built into such a shunt which function to begin or cease shunt at specific local conditions. These are 'onset' or 'offset' thresholds. In each case, for example, pressure or flow acts to change the effective shunt lumen size (open, close, other). The opening, if made highly nonlinear, can affect a 'snap open' or 'snap closed' result, effectively being a gating function of flow, pressure, or another regulated parameter.

The purpose of adaptive shunting is to protect organs or biologic tissues from pressure or flow damage. This protection may be conferred by limiting pressures at either the source or receiving end of the connection. For example, if the source of flow is the right heart, this chamber cannot sustain prolonged elevated pressures and a "bleed off" shunt could be used to drop pressures which are approaching or exceeding a specified threshold value. Such a threshold value may be variable and inherently built into the device such that the pressure-flow relationship is linear, or nonlinear of any sort to accommodate physiologic benefit. Similarly, elevated right heart pressures yield elevated pulmonary pressures which can damage lung tissue, causing scar and fibrosis with long-term catastrophic results if left unchecked. A response to increased pressure conditions during exercise may be possible with an adaptive shunt design as well.

Adaptive shunts may thus be used as regulators for a pressure-flow relationship and would thus be made to function in an "autoregulatory mode". This feature is useful to maintain healthy and safe pressures (for example) or other parameters by shunting flow (or other parameters) into lower resistance, or higher compliance chambers or channels. An example of this is right heart and pulmonary hypertension which severely damages the right atrium, right ventricle and plumber tissues due to elevated pulmonary vascular resistance. By shunting blood flow partially into a compliant, low-pressure chamber such as the superior vena cava, pressures are reduced simultaneously both the lungs and the right heart are protected from elevated pressure, a phenomenon facilitated by flow shunting.

In one example an adaptive shunt would shunt more blood to the low-pressure chamber at higher pressures, feeding back on the source and lowering source pressure as it attempts to increase. Similarly, if pressure drops to lower levels the shunt will contract and shunt less blood from high-to-low pressure chamber, hence preventing the pressure to drop too low which would potentially dangerously reduce cardiac output in the case of pulmonary artery to vena cava shunt.

Another advantage of using a low-pressure chamber such as the vena cava is that it is highly compliant. A sudden bolus of blood from a hyperactive right heart will have its pressure effects minimized by compliance features of the low-pressure chamber without compromising total flow.

As noted, low pressure will shunt less flow, and thus increased cardiac output above what would have been achieved otherwise had the shunt remained large. The protective effect on sensitive organs is markedly better with an adaptive shunt.

These flow-control mechanisms may incorporate a Grommet system which expands as the device undergoes plastic expansile or contractile deformation and opens (closes) a lumen in proportion to internal tube or planar pressure.

Allometric scaling can be applied to these devices so that the concept can be used in small systems such as infants (palliative procedures for temporary surgery in the case of artery to prove vena cava) or scaled large chambers such as fully-grown adults.

More than 1 shunt connection may be made in this concept, where an ensemble of devices can be placed to amplify their effect. In this ensemble not all devices need have the same pressure flow adaptability, thus markedly increasing the potential dynamic range across pressure and flow spectra.

Various adaptive flow-control mechanisms for use with the various shunt designs are shown in FIGS. 16-50. FIGS. 16-17 show a mechanism 60 that incorporates struts 62 that spread from a closed position (FIG. 16) to an open position (FIG. 17) when subjected to flow pressure.

FIGS. 18-19 show a mechanism 64 that uses vanes 66 that rotate from a closed position (FIG. 18) to an open position (FIG. 19) when subjected to flow pressure.

Figure 20:
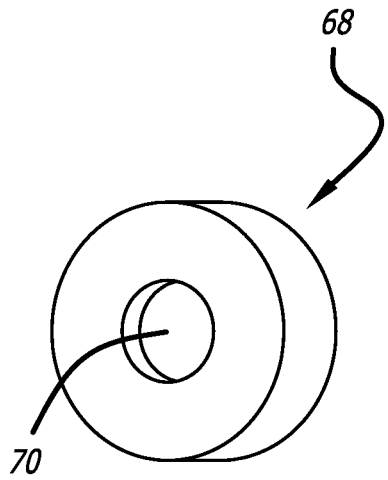
FIG. 20 is a perspective view of an embodiment of the invention in a closed or constricted configuration.
Figure 21:
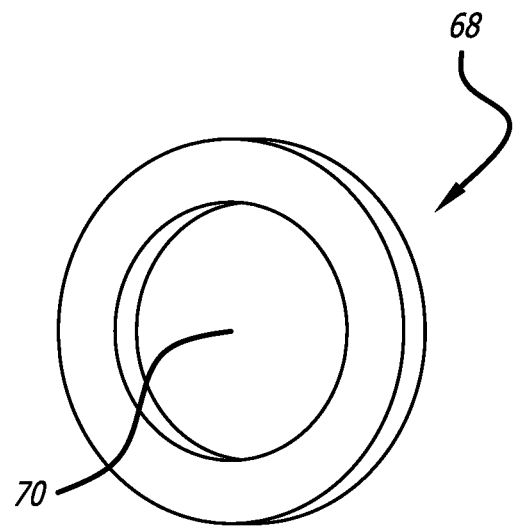
FIG. 21 is a perspective view of the embodiment of FIG. 20 in an open configuration.
Figure 22:
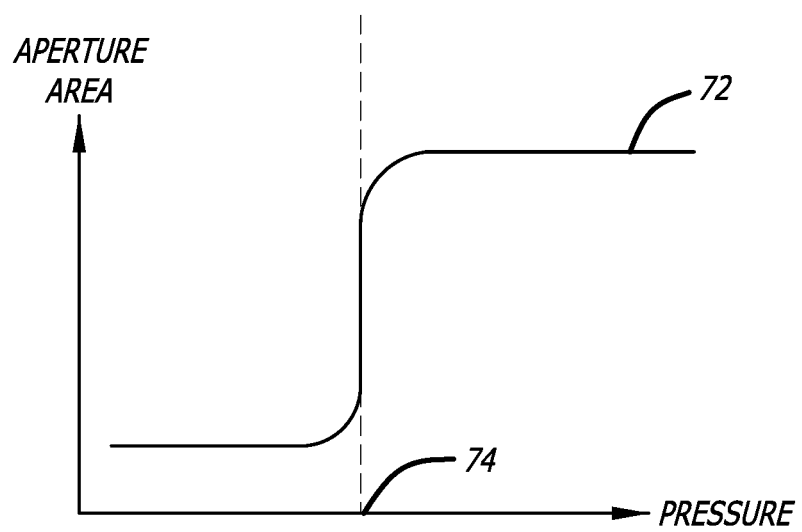
FIG. 22 is a graph of aperture area vs pressure for some of the embodiments of the invention.

FIGS. 20-21 show a mechanism 68 that is essentially an elastic disc or toroid that defines an aperture 70 that spreads from a closed or small opening (FIG. 20) to a larger opening (FIG. 21) when subjected to flow pressure. As seen in the graph of FIG. 22, which graphs the area 72 of the aperture 70 as pressure increases, the mechanism 68 may exhibit a snap-like behavior in which it reacts quickly, snapping to the open position when a threshold pressure 74 is met.

Figure 23:
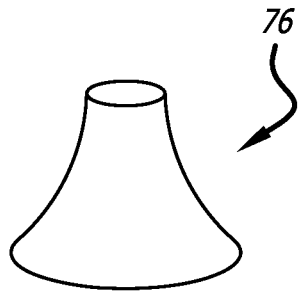
FIG. 23 is a perspective view of an embodiment of the invention in a closed or constricted configuration.
Figure 24:
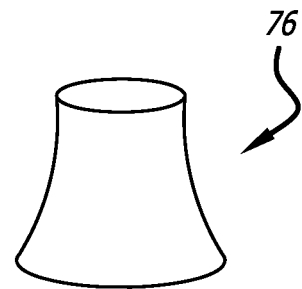
FIG. 24 is a perspective view of the embodiment of FIG. 23 in an open configuration.

FIGS. 23-24 show a conical mechanism 76 that stretches to a larger diameter when subjected to fluid pressure.

Figure 25:
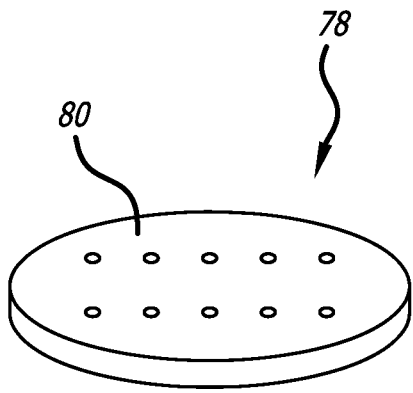
FIG. 25 is a perspective view of an embodiment of the invention in a closed or constricted configuration.
Figure 26:
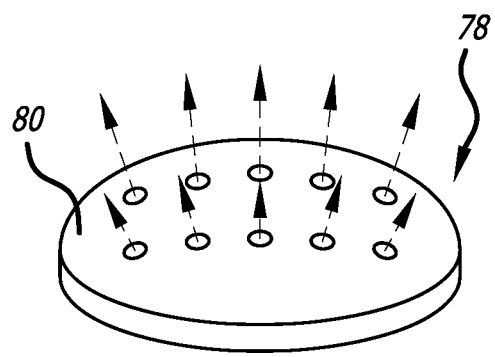
FIG. 26 is a perspective view of the embodiment of FIG. 25 in an open configuration.

FIGS. 25-26 show an elastic disc 78 having several holes 80 formed therein, such as laser-cut holes, which effectively allow no flow to pass through them (FIG. 25) until the elastic disc is stretched due to pressure (FIG. 26). The stretching opens the holes, allowing pressure to be relieved, at which time the elastic nature of the disc closes the holes. The holes or hole patterns may take on many different forms or mosaics, depending on the desired resulting flow characteristics.

Figure 27:
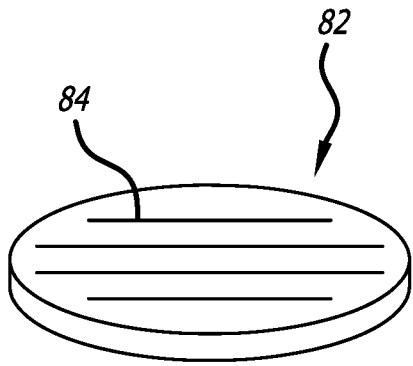
FIG. 27 is a perspective view of an embodiment of the invention in a closed or constricted configuration.
Figure 28:
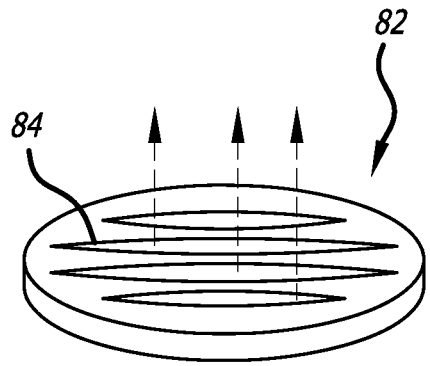
FIG. 28 is a perspective view of the embodiment of FIG. 27 in an open configuration.

FIGS. 27-28 depict a flat substrate or disc 82 that includes one or more slits 84 that spread and open when subjected to fluid pressure.

Figure 29:
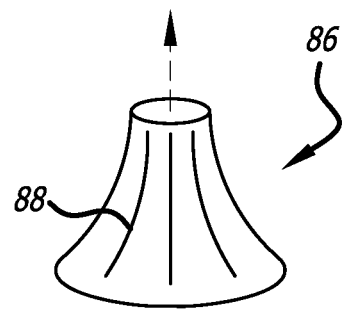
FIG. 29 is a perspective view of an embodiment of the invention in a closed or constricted configuration.
Figure 30:
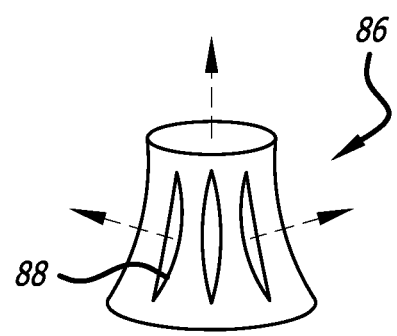
FIG. 30 is a perspective view of the embodiment of FIG. 29 in an open configuration.

FIGS. 29-30 depict a conical device 86 that uses slits 88 that spread when subjected to fluid pressure to increase the flow through the lumen and to allow flow to escape through the sidewalls of the device.

Figure 31:
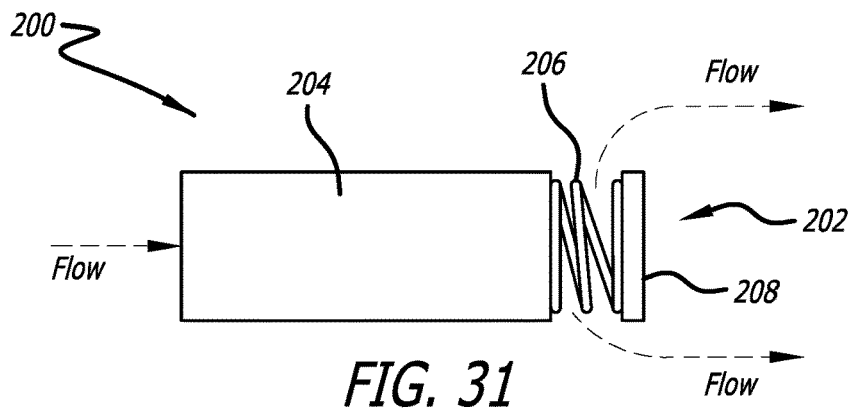
FIG. 31 is a side elevation of an embodiment of a device of the invention.
Figure 32:
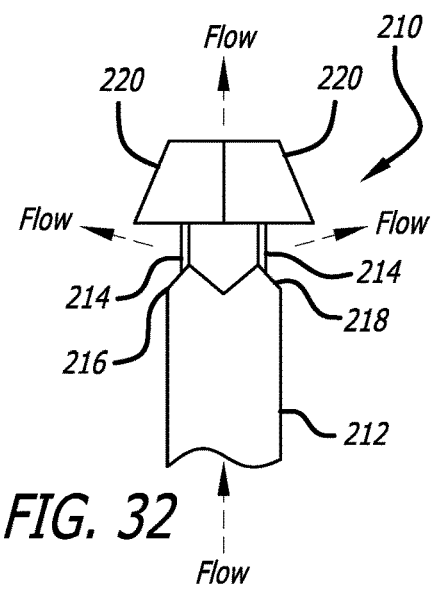
FIG. 32 is an elevation of an embodiment of a device of the invention.

In some embodiments, there is a direct relationship between the pressure drop across the shunt and the flow rate through the shunt. As the pressure drop increases, the flow rate increases. Referring to FIG. 31, there is shown a shunt 200 with a flow control device 202 attached to an end of the shunt body 204. The shunt body 204 may be a stent. The flow control device 202 includes a spring 206 and a disc 208. The spring 206 is attached to the distal end of the body 204 and the disc 208 is attached to the distal end of the spring 206. The disc is impermeable and may be flexible. Non-limiting examples of disc designs include flexible covered laser cut disc, polymer/fabric disc with thick rim or Nitinol wire reinforced rim; rigid biocompatible disc; etc.). The spring is shape set in the unstretched, tight pitch configuration. As the pressure gradient across the stent or shunt increases, the drag of the fluid across the disc increases and exerts a tensile force, lengthening the spring. The disc could also have a small hole if minimal flow desired in the "closed" state. The spring could also be set to a shape that has a small gap between the wire wraps in order to perform as a filter.

Figure 33:
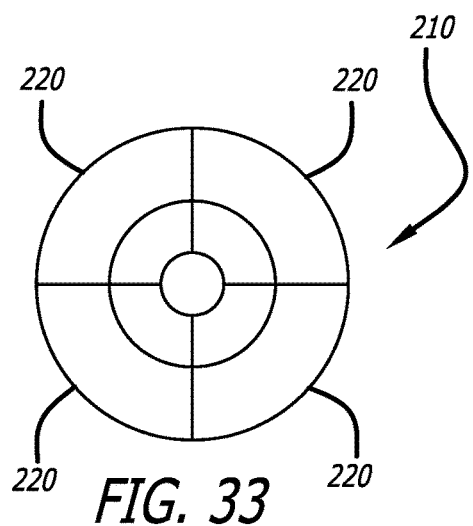
FIG. 33 is an end view of the embodiment of FIG. 32.
Figure 34:
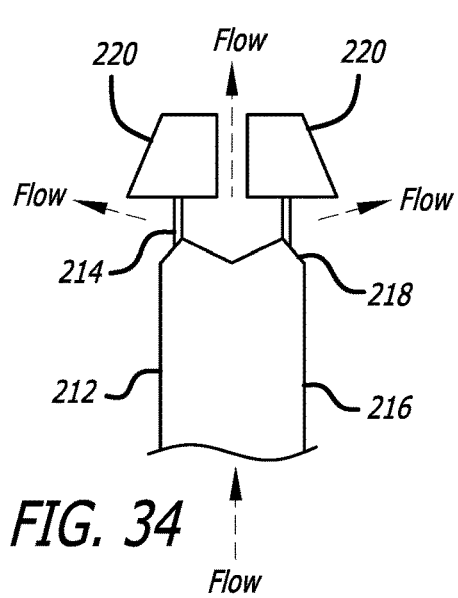
FIG. 34 is an elevation of the embodiment of FIG. 32 in an open configuration.
Figure 35:
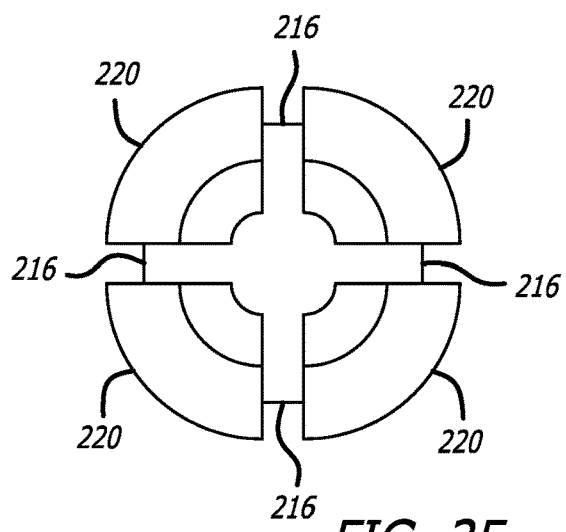
FIG. 35 is an end view of the embodiment of FIG. 34.

FIGS. 32-35 depict a device 210 that includes a covered stent 212 with uncovered spring members 214 extending from a distal end 216 of the stent 212. The spring members 214 are attached to outflow apices 218. The distal end of each spring member 214 is attached to a wedge-shaped impermeable and/or collapsible flap 220. The flaps are all shape-set to cover the outflow of the shunt 210. At low pressures, the flaps 220 restrict or prevent flow. At higher pressures, the flaps are forced open, allowing additional flow. This may be seen by comparing the flow arrows between FIGS. 32 and 34. FIGS. 33 and 35 show a top plan view in a closed and open position, respectively.

The embodiments of FIGS. 31-35 are advantageous because the variable shunting mechanism is not dependent on straining of polymers, which have difficulty maintaining consistent mechanical properties. Preferably, straining occurs in areas of the devices that utilize bare metal materials such as Nitinol.

Figure 36:
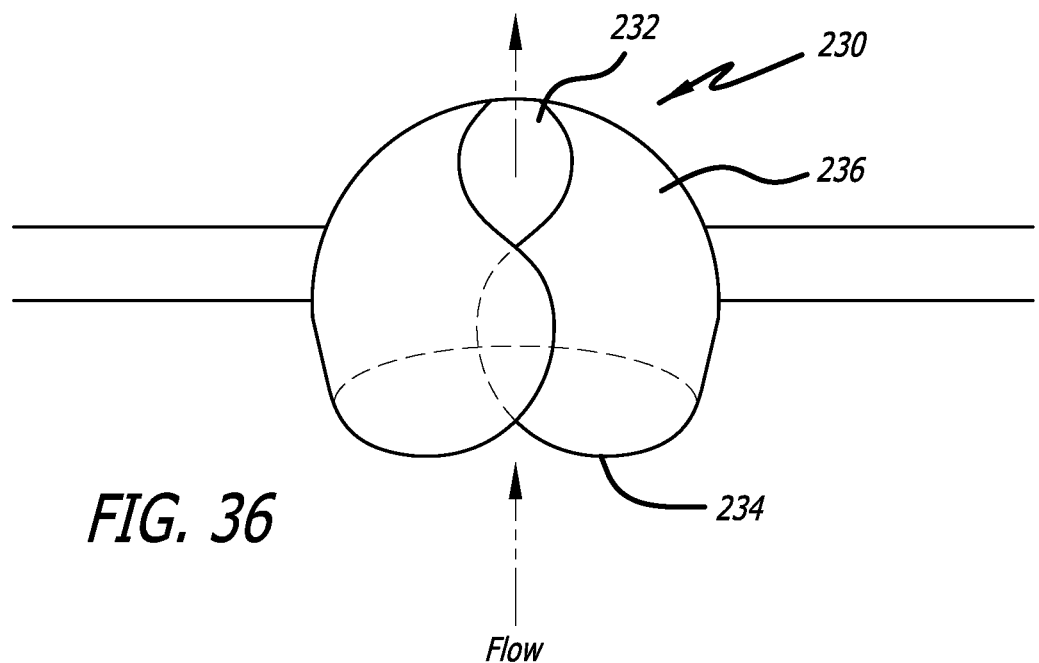
FIG. 36 is a perspective view of an embodiment of the invention in a closed or constricted configuration.
Figure 37:
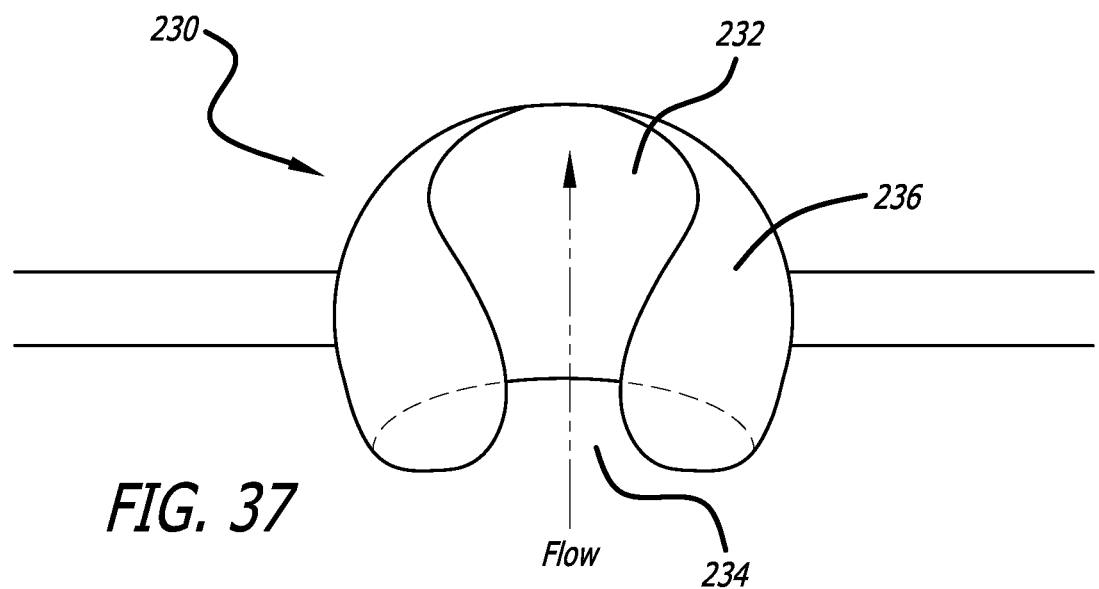
FIG. 37 is a perspective view of the embodiment of FIG. 36 in an open configuration.

FIGS. 36 and 37 show a slotted or overlapped compliant collar 230, which may be used in conjunction with any of the disclosed devices or used as a stand-alone device. The collar 230 has a narrow or closed end 232, a wide or open end 234 and an overlapping body 236. The collar 230 is shape-set such that the narrow end 232 has a small ID, which may be completely closed. As the pressure gradient increases, the overlapping body 236 expands and opens up, as best shown in FIG. 37, increasing the ID of the end 232, thereby allowing an increased flow rate. Other embodiments of this device could incorporate a slotted distal end, a conical body and slotted distal end, a Nitinol body with a compliant polymer covering, folded polymers instead of slots, and the like.

Figure 38:
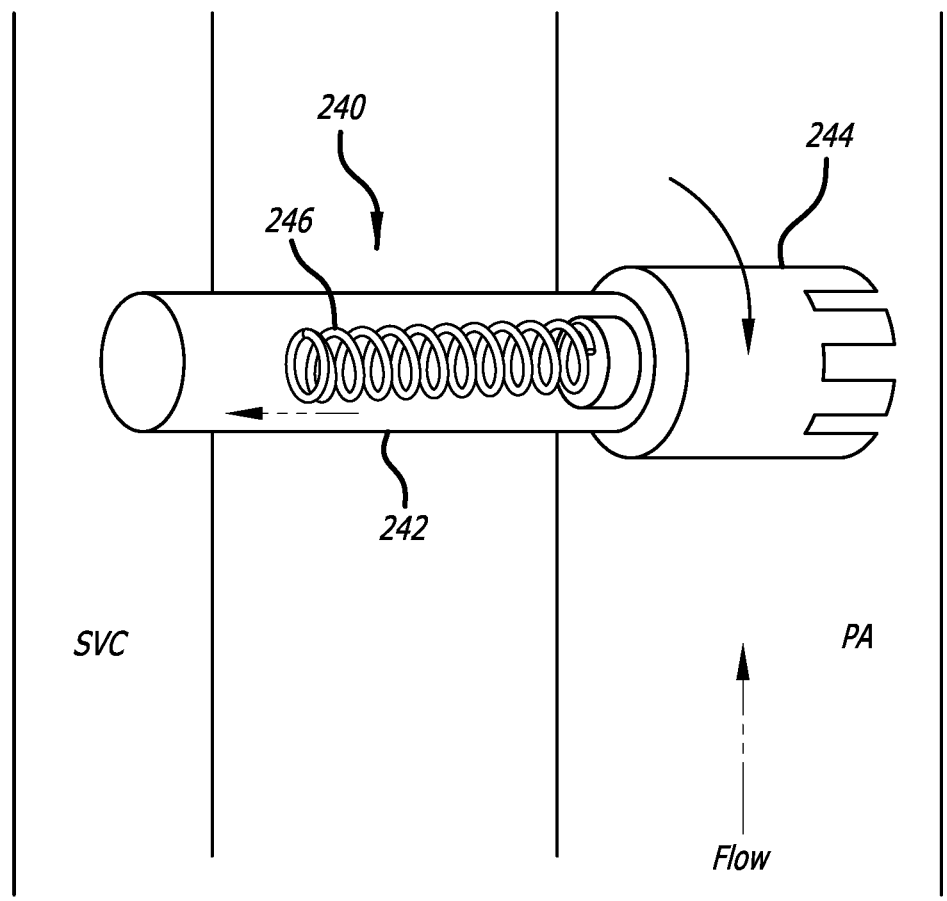
FIG. 38 is a perspective view of an embodiment of a device of the invention.

FIG. 38 shows a Touhy Borst style shunt 240. The shunt 240 has a compliant tube body 242 having an inflow side with a wheel mechanism 244 that spins in response to fluid flow. As the wheel 244 spins, it opens a lumen through the tube 242 by axially decompressing the tube. During lower flow, a torsional spring 246 connected to the wheel 244 recloses the device. One application of the device 240 creates a shunt joining the pulmonary artery PA to the superior vena cava SVC. The wheel 244 spins during systolic flow in the PA, causing the tube 242 to open and relieve excess pressure into the SVC. During diastolic flow, the spring 246 closes the tube and prevents leakage between the PA and the SVC. The ends of the device 240 are shown as extending into the bodily chambers, in this case the SVC and the PA. In addition to allowing the wheel 244 to spin, extending the device ends into the chambers helps prevent the lumen from getting clogged due to ingrowth, etc.

Figure 39:
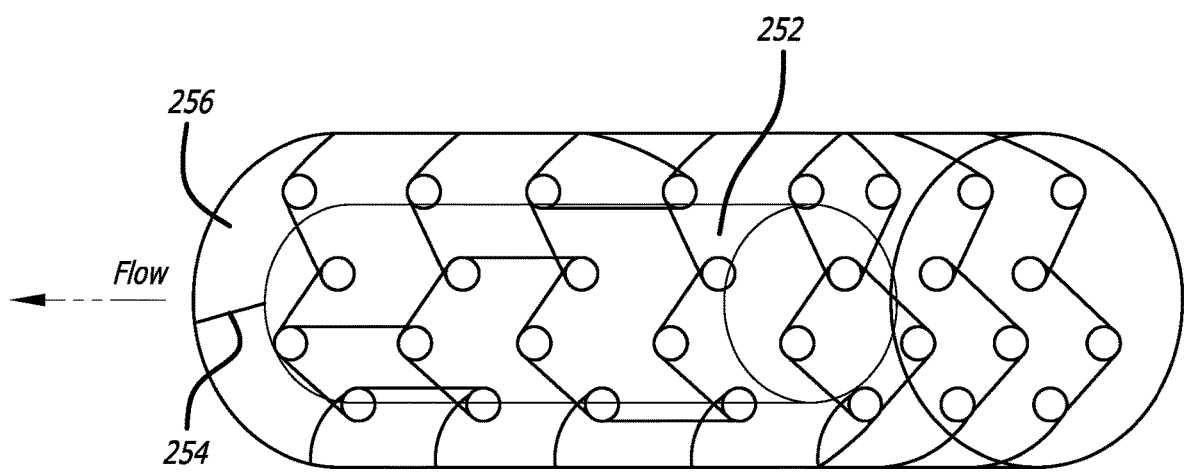
FIG. 39 is a perspective view of an embodiment of a device of the invention.

FIG. 39 shows an auxetic stent shunt 250 with a spacer 252 fixed to the shunt ID 254 at the outflow 256. The spacer is a cylindrical element that is attached to the auxetic stent. The cylindrical element, when exposed to a differential pressure, exerts a tensile load on the stent. As the tensile load is applied, the auxetic stent expands in diameter. This expansion in diameter modulates and changes the resistance of the shunt to flow, changing the volume flow rate of the shunt in response to pressure.

The auxetic stent 250 is designed such that under axial tension, the stent 250 expands radially. As the pressure gradient increases across the shunt 250, the spacer 252 moves toward the outflow, thus exerting an axial tensile load on the stent 250 and causes the stent 250 to radially expand. As the pressure gradient decreases, the stent 250 contracts radially.

Figure 40:
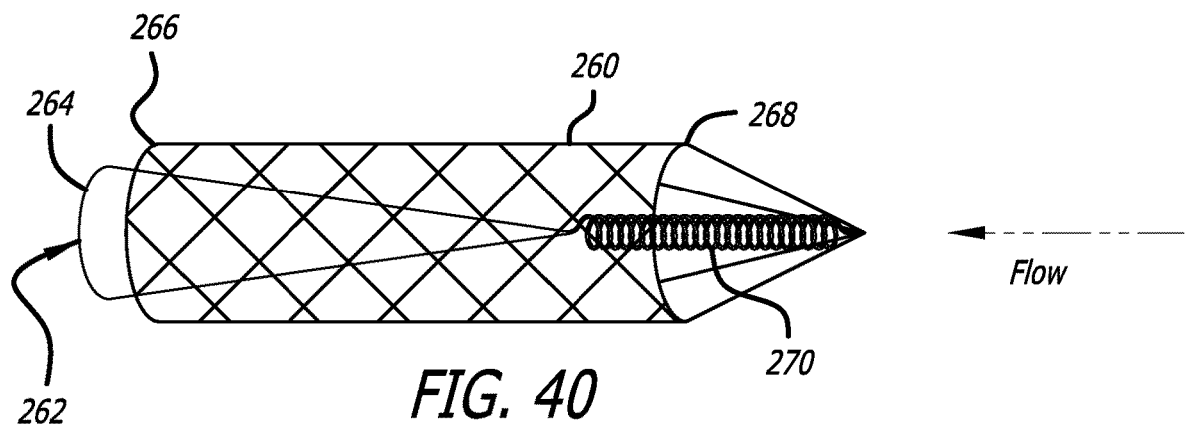
FIG. 40 is a side elevation of an embodiment of a device of the invention.
Figure 41:
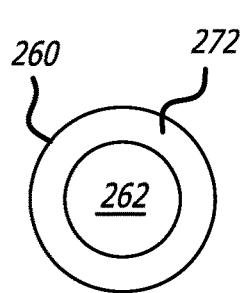
FIG. 41 is an end view of the embodiment of FIG. 40 is a low-flow configuration.
Figure 42:
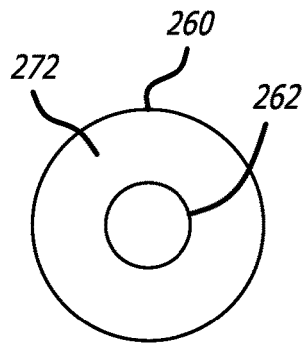
FIG. 42 is an end view of the embodiment of FIG. 40 is a medium-flow configuration.
Figure 43:
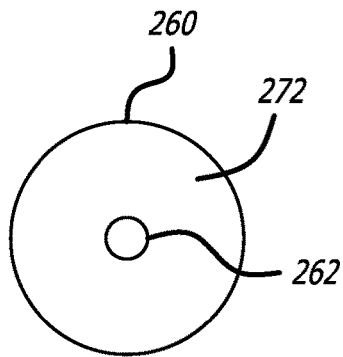
FIG. 43 is an end view of the embodiment of FIG. 40 in a high-flow configuration.

FIG. 40 shows a covered stent 260 with a variable OD spacer 262 in the ID of the stent 260. The larger OD side 264 of the spacer 262 is at the shunt outflow 266 and the OD progressively decreases towards the inflow 268. A spring 270 connecting the spacer 262 and the shunt 260 forces the large OD side 264 of the spacer 262 to fill the shunt outflow 266. As the pressure gradient increases, the spacer 262 is forced towards the outflow 266, effectively increasing the cross-section area of the outflow opening 266, thus allowing increased flow. This is depicted in FIGS. 41-43, which show an end view of the space 272 that exists between the stent 260 and the spacer 262. In FIG. 41, the spacer is in a low-flow position in which the spacer 262 blocks the outflow of the stent 260, resulting in a smaller space 272 for flow. FIG. 42 shows a medium-flow condition in which the spacer 262 is displaced from the stent 260, creating a greater space 272 for flow. FIG. 43 shows a maximum displacement position of the spacer 262, creating maximum space 272 for flow between the spacer 262 and the stent 260.

Figure 44:
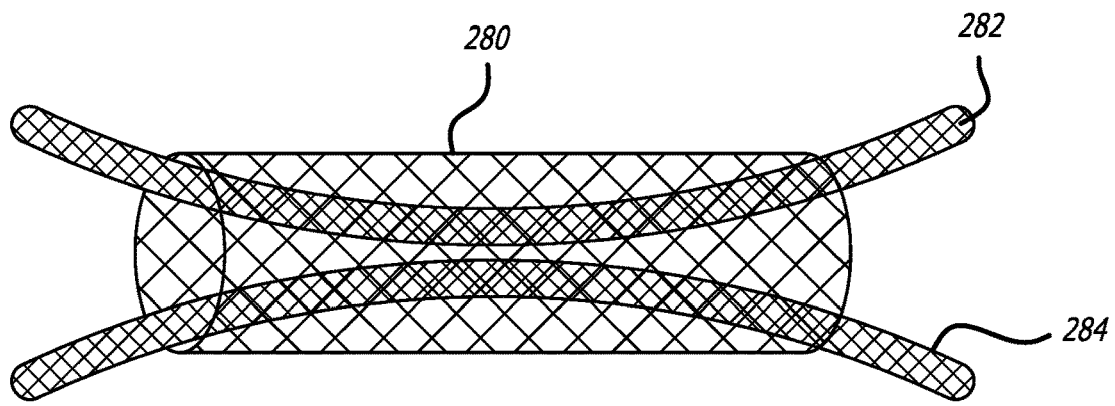
FIG. 44 is a perspective view of an embodiment of the invention.

FIG. 44 shows a covered stent shunt 280 with two expandable braided structures 282 and 284 attached to an interior of the shunt 280. The braided structures 282 and 284 are shape-set to occlude the shunt 280. As the pressure gradient across the shunt 280 increases, the braided structures 282 and 284 are forced apart to allow flow through the shunt 280.

Some of the stent designs of the present invention have flow control mechanisms that prevent flow until a targeted pressure range is achieved. An application of this would, for example, be in a cardiac setting. Cardiac output is preserved until a danger pressure is reach at which point the flow control mechanism opens to relieve pressure.

Figure 45:
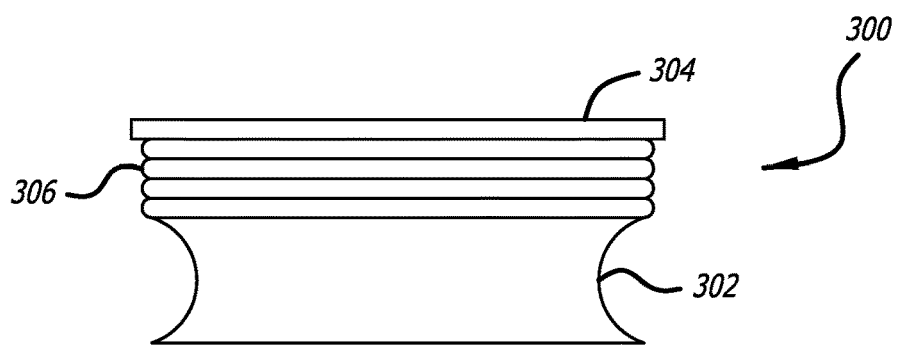
FIG. 45 is a side elevation of an embodiment of a device of the invention.
Figure 46:
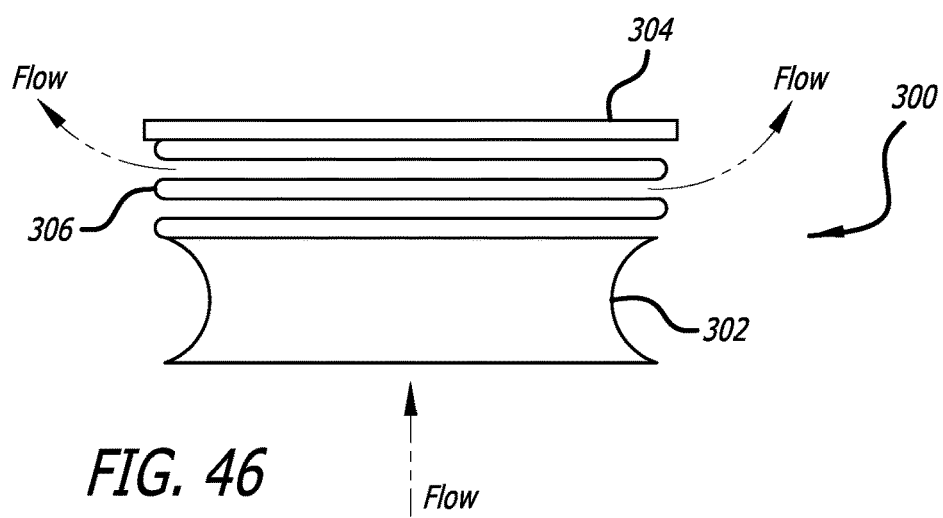
FIG. 46 is a side elevation of an embodiment of a device of the invention.

FIG. 45 shows a device 300 that remains closed until a threshold pressure is reached. The device 300 includes a body 302 and a cap 304 connected to the body 302 with a spring 306 at an outflow end of the body 302. The spring 306 keeps the cap 304 closed during diastolic pressures. Higher systolic pressures cause the spring 306 to stretch and allows blood to flow through the spring 306, thereby releasing pressure, as shown in FIG. 46.

Figure 47:
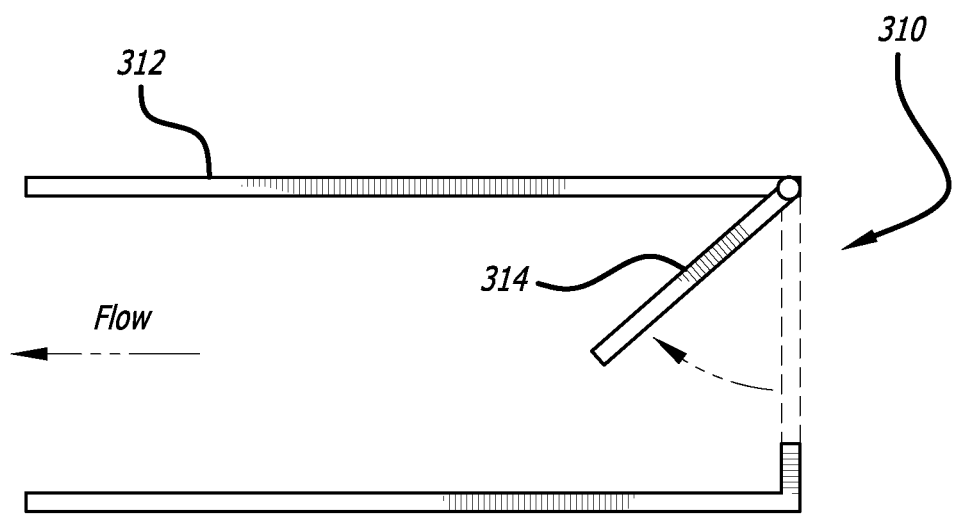
FIG. 47 is a side elevation of an embodiment of a device of the invention.

FIG. 47 is a shunt 310 that includes a covered stent 312 with a hinged flap 314 at an inflow end. The hinged flap 314 is spring-loaded to a closed position that must be overcome by a threshold pressure before the flap opens to relieve pressure.

Figure 48:
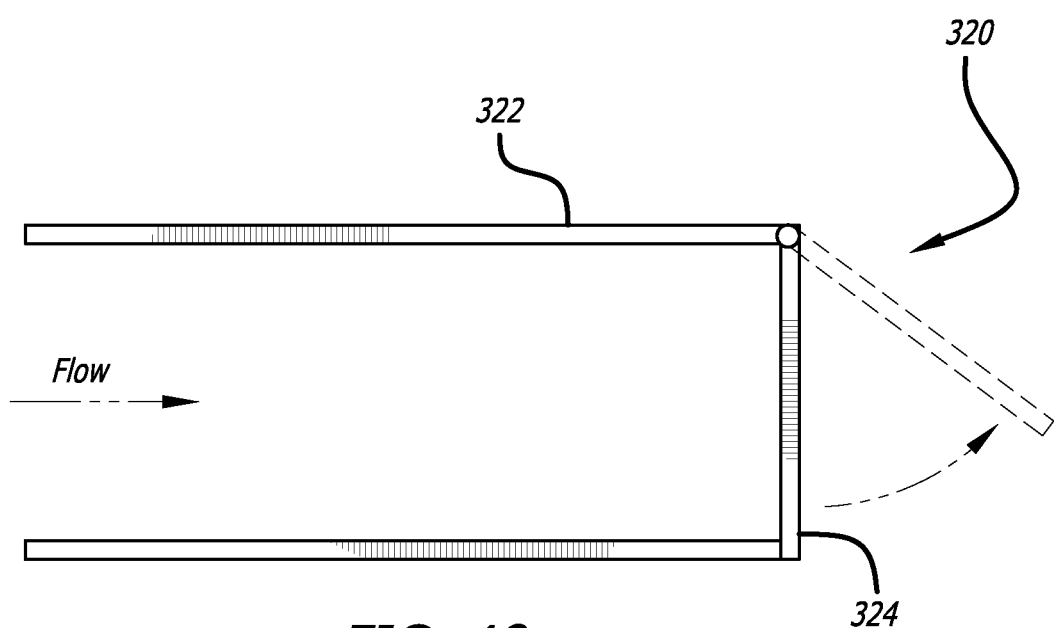
FIG. 48 is a side elevation of an embodiment of a device of the invention.

FIG. 48 is another embodiment of a shunt 320 that includes a covered stent 322 with a hinged flap 324. The shunt 320 has the hinged flap 324 at the outflow end of the stent 322. The hinged flap 324 is spring-loaded to a closed position that must be overcome by a threshold pressure before the flap opens to relieve pressure.

Figure 49:
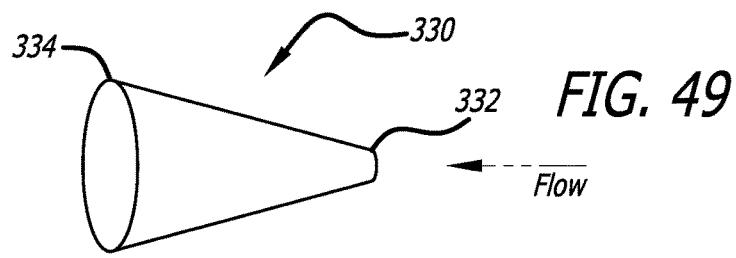
FIG. 49 is a perspective view of an embodiment of a device of the invention.

Some embodiments of shunts may have pressure-driven flow mechanisms that minimize flow velocities in order to prevent certain conditions such as hemolysis. FIG. 49 shows a covered stent shunt 330 shaped with a conical ID, such that the smaller ID end 332 is inflow and the larger ID end 334 is outflow. During shunting, the flow velocity is decreased as the fluid passes through to the outflow end 334.

Figure 50:
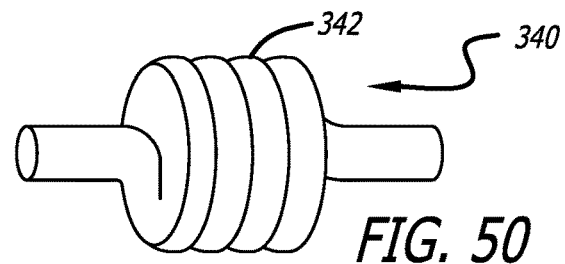
FIG. 50 is a perspective view of an embodiment of a device of the invention.

FIG. 50 shows a shunt 340 with a coiled section 342. The shunt 340 is a covered stent or tube that follows a coiled trajectory. The coiled section 342 maximizes the length for flow through the stent. This longer length of flow creates impedance and reduces flow velocity. A variation of this concept is to have the stent follow any tortuous path to increase impedance. Additional features, such as the placement of resistive flow disruptor within the stent could also be implemented.

Directional Shunting

Directional shunting refers to the manipulation of the flow direction and quality as the fluid or gas passes through the device.

By way of introduction and convention, FIGS. 51-55 show different forms of directional shunting. Substrate 350 is used to represent a generic featureless device that manipulates the incoming flow, as represented by the arrows.

Figure 51:
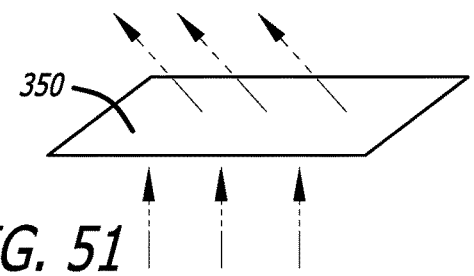
FIG. 51 is a perspective view of a flow pattern of the invention.

FIG. 51 shows a redirection of flow such that the direction of flow leaving the device is angled relative to the flow entering the device.

Figure 52:
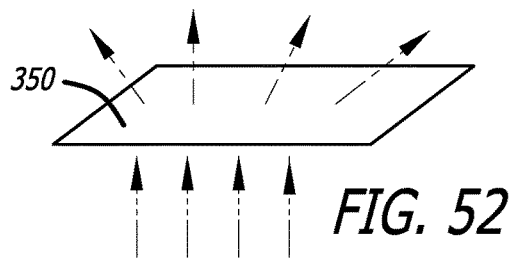
FIG. 52 is a perspective view of a flow pattern of the invention.

FIG. 52 shows an example of flow scattering. Laminar flow enters the device and is scattered in various directions upon leaving the device.

Figure 53:
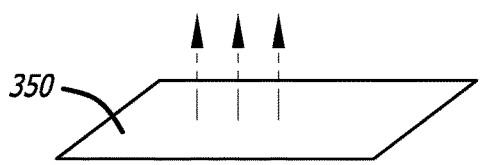
FIG. 53 is a perspective view of a flow pattern of the invention.
Figure 54:
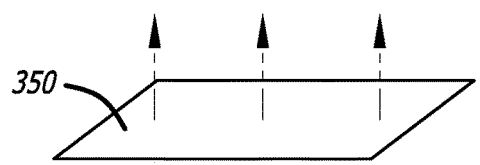
FIG. 54 is a perspective view of a flow pattern of the invention.

FIG. 53 shows an example of flow concentration. The outgoing flow is concentrated relative to the incoming flow. The flow may be a spray whereby the whole is effectively a nozzle sending blood inappropriate directions at appropriate velocities to match the needs of a receiving chamber. This feature may also create or lira it turbulent flow to dissipate energy, or to prevent 'jetting' which is undesirable when impinging at a distal site and may cause jet-induced tissue damage FIG. 54 shows an example of flow-softening. Laminar flow enters and leaves the device, but the outflow is softer and less concentrated than the incoming flow.

Figure 55:
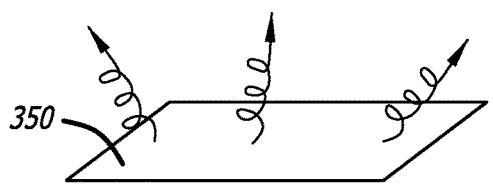
FIG. 55 is a perspective view of a flow pattern of the invention.

FIG. 55 shows an example of a device that softens flow by creating a turbulent outflow. The turbulence would dissipate energy from a stream and increase safety in the receiving chamber due to a lowered internal and potential energy status of the flow jet.

In some embodiments, shunts are designed with blood flow direction in mind for advantageous results. For example, in the case of shunting from the PA to the SVC, shunts are provided that pull flow from the main PA branch instead of the RPA (Right Pulmonary Artery) branch.

The devices and hole(s) they have capability of directing flow in specific spatial orientation with the purpose of filling a chamber which otherwise may not fill or may not see higher flow. A single or else a multiplicity of directions is considered. An example of the need for this would be in a left atrial appendage shunt where a fluid jet would be directed toward the apex appendage, keeping flow maximized and preventing flow stagnation which promotes thrombus formation.

To prevent reverse or inverted flow a valve structure such as flap or other one-way mechanism may be employed to partially prevent fluid for blood under from reversing its direction, while preserving shunt function with beat to beat shunting to prevent stasis and thrombosis.

The device and its spring constant may be made nonlinear so that it is activated in more of a binary fashion which occurs at a threshold. Hysteresis may be designed in the spring features so that positions of activation and deactivation corrective thresholds. Another method of designing beat to beat expandability is to use an elastomeric polymer as a covering or a zone of expansion. This would impart expansion during systole and contraction during diastole, both imparting greater flow during systole, and dampening the systolic pressure.

A bulbous elastomeric segment may be designed into the distal segment of the shunt creating a volumetric shunt The flow may be made to perform channeling, so it is directed and multiple channels directions a single or multiple orifice connector with nozzle like features.

Figure 56:
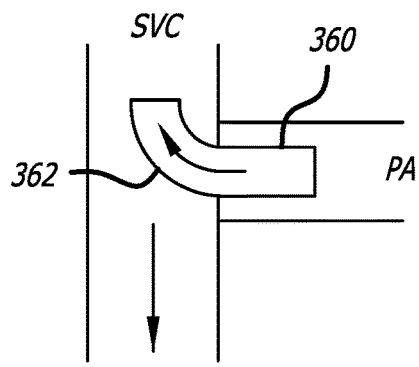
FIG. 56 is a plan view of an embodiment of a device of the invention.

Referring to FIG. 56, there is shown a shunt 360 with a bend 362 that allows the shunt 360 to direct flow in a superior direction in the SVC. The potential benefit of this is that it reduces the right ventricle preload and protects the right atrium from potential arterial fibrillation.

Figure 57:
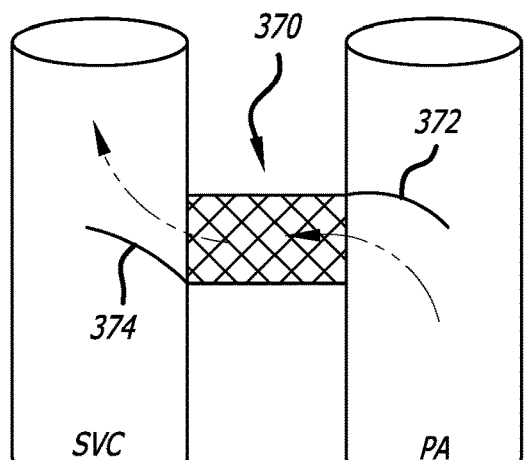
FIG. 57 is a perspective view of an embodiment of a device of the invention.

FIG. 57 shows a covered stent 370 with deflectable flaps on an inflow side 372 and an outflow side 374. The inflow flap 372 opens and closes in response to PA flow and is thus an adaptive or variable shunt. The outflow flap 374 creates a directional shunt as it directs the flow in a superior direction in the SVC.

Figure 58:
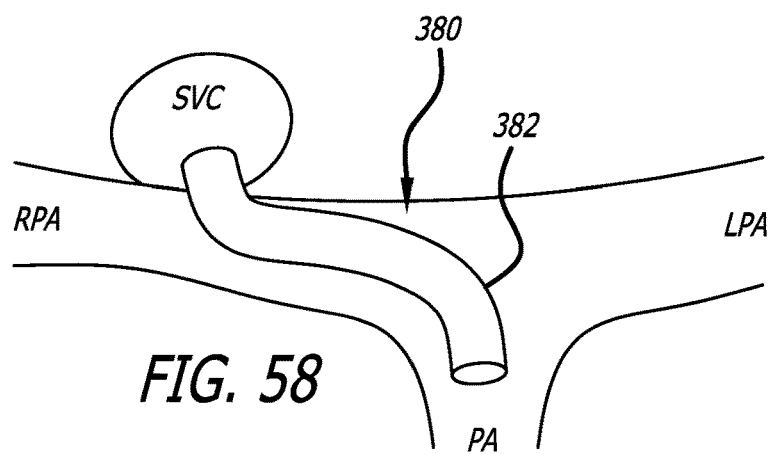
FIG. 58 is a perspective view of an embodiment of a device of the invention.

Based on human CT's, the SVC most often crosses the PA at the RPA. Shunting in this location may result in uneven blood supply to the left and right lungs. FIG. 58 depicts a variable shunt 380 with deflectable arms 382 to create flow rate variability and outflow directionality. The shunt 380 is a longer, flexible, covered shunt with inflow located in the main PA and then crosses to the SVC in the RPA. This configuration ensures more even shunting from each of the lungs' blood supplies.

Figure 59:
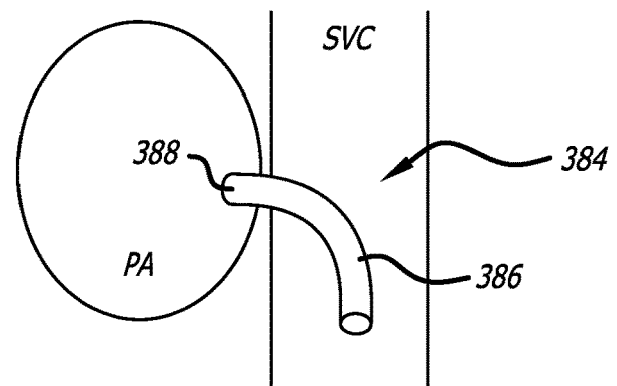
FIG. 59 is a perspective view of an embodiment of a device of the invention.

FIG. 59 depicts a shunt 384 with a compliance element 386 that extends into the SVC. This covered stent shunt 384 has a long compliant extension 386 that provides a higher compliance than a portion 388 that resides in the PA. In one embodiment, the compliant chamber is closed to the SVC. In systole, the compliant section takes in PA volume and in diastole, ejects the volume back into the PA. The compliant chamber would reduce PA pulse pressure and improve cardiac output when compared to a simple shunt. This is beneficial over the Aria CV concept because it would not require the periodic recharge of the balloon and the device does not cross any native valves. In another embodiment, the compliant chamber would have an outflow end in the SVC. The outflow would be valve-controlled to be open at higher PA pressures and closed during lower PA pressures. This would result in even lower PA pulse pressure and lower mean PA pressure. This may reduce cardiac output.

Figure 60:
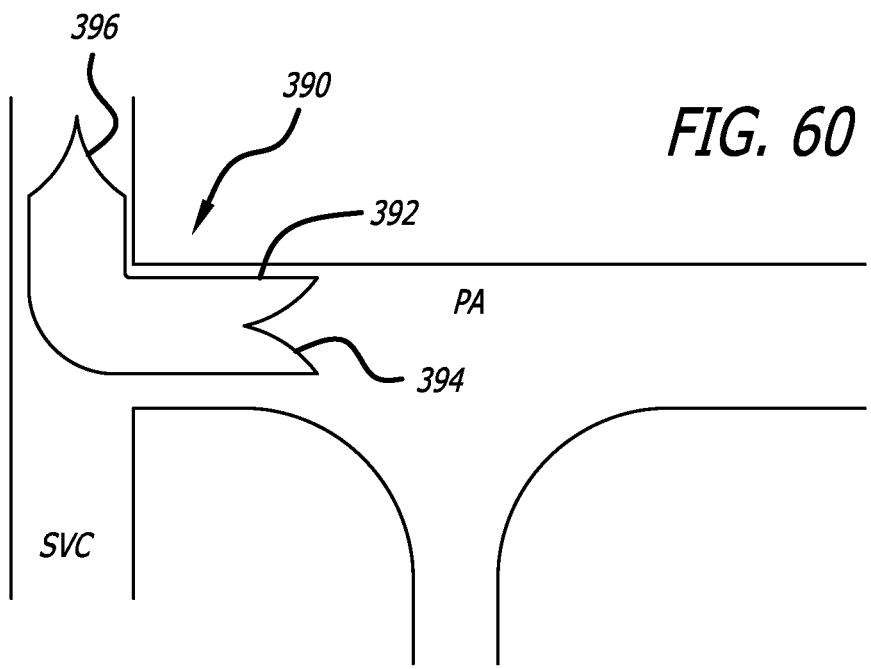
FIG. 60 is a plan view of an embodiment of a device of the invention.

FIG. 60 shows a bi-valve shunt 390 with a compliance element 392 that extends into the SVC. This variation includes valve 394 at the inflow, and a valve 396 at the outflow. The outflow valve is set to open at a pressure below a peak PA pressure, but well above the PA diastolic pressure. The inflow would be set to open slightly above the PA diastolic pressure. This would provide potentially reduced PA pulse pressure, reduced mean PA pressure, and still maintain cardiac output.

Figure 61:
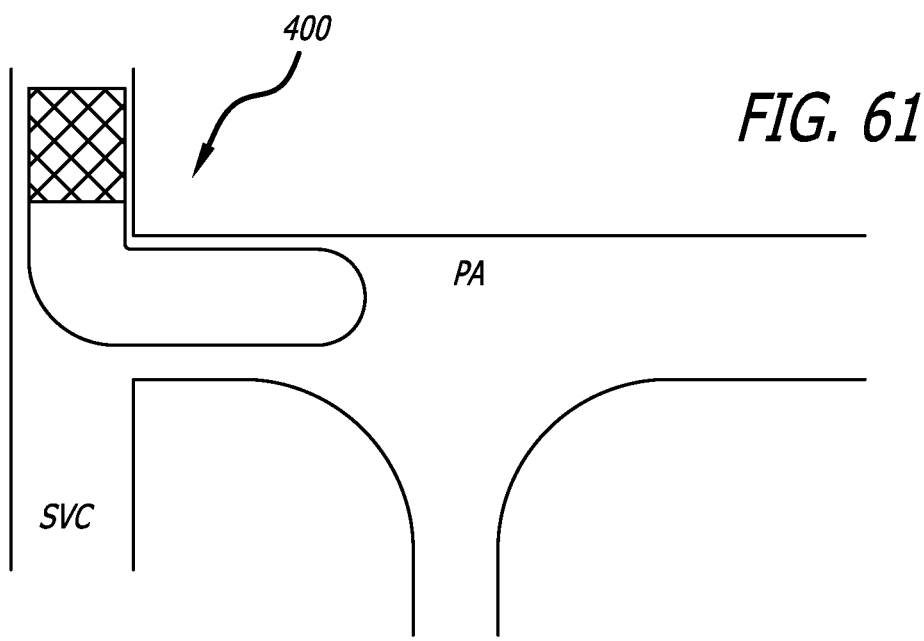
FIG. 61 is a plan view of an embodiment of a device of the invention.

FIG. 61 shows a closed dual compliance chamber device 400. This device is similar to device 384 of FIG. 59 except the device is fully closed on the inflow side. The chamber in the PA would be more compliant than the chamber in the SVC. The closed device could be filled with either a compressible or non-compressible fluid, such as saline. In systole, the SVC chamber takes in PA volume and in diastole, ejects the volume back into the PA chamber. This device would reduce PA pulse pressure and improve cardiac output, as compared to a simple shunt. This is beneficial over the Aria CV concept because it would not require the periodic recharge.

Some pressure driven variable shunts of the invention are closed at low pressures (diastole) and open at mid-range pressures and high pressures. These devices allow for variable shunting that would help preserve cardiac output by preventing shunting during diastole, and also prevent potential hemolysis at high peak PA pressures.

Figure 62:
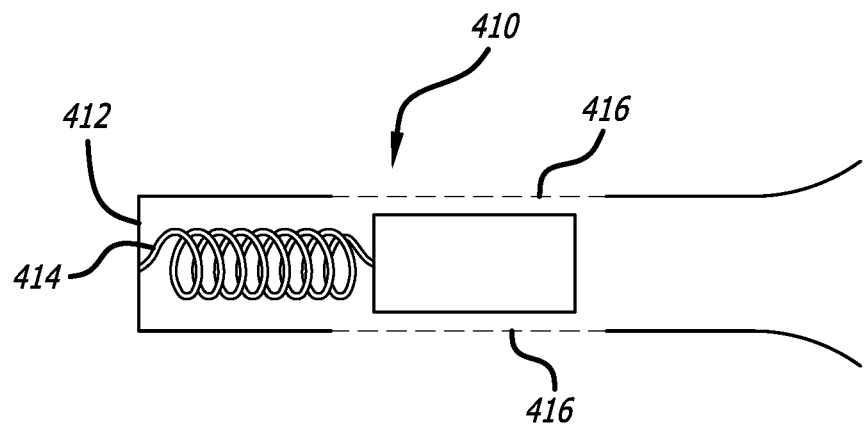
FIG. 62 is a plan view of an embodiment of a device of the invention.

FIG. 62 shows a covered stent shunt 410 with a spacer 412 on the outflow side driven by a spring 414. There is a plurality of hole sets 416 on the side wall of the covered stent. At low pressures only one set of holes is exposed. As pressure increases, the output pressure is controlled based on a combination of side holes exposed and the number of spacers used.

Figure 63:
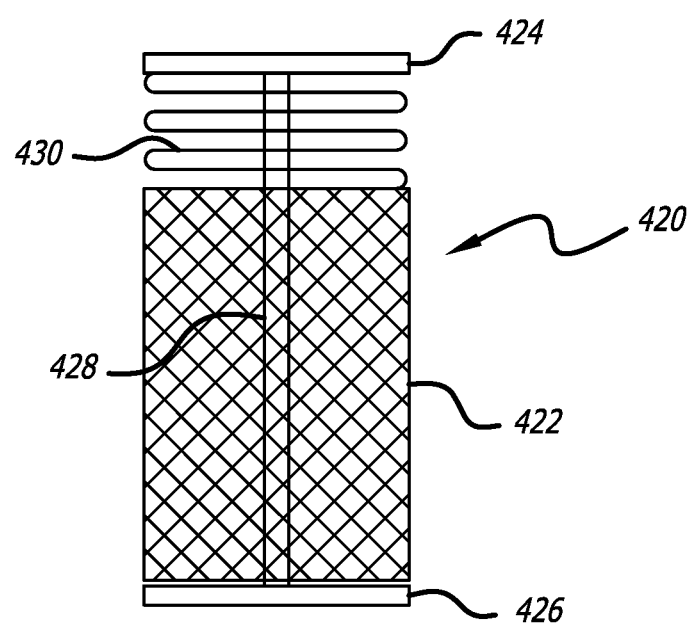
FIG. 63 is a plan view of an embodiment of a device of the invention.

FIG. 63 shows a device 420 that includes a body 422 with ends that are selectively covered by stoppers 424 and 426. The stoppers are connected by a shaft 428 that is slightly longer than the body 422. The stopper 424 is biased to an open position by a spring 430. If the pressure through the device increases sufficiently, the flow will impact an inside surface of the plunger 426, and combined with the pressure on the outside surface of the plunger 424, the spring force will be overcome and the plunger 424 will seat, blocking flow through the device, while allowing pressure to be relieved therefrom by flowing around plunger 426.

Methods and Applications

Having discussed the various device of the invention, discussion now turns to methods implementing the advantages provided by the devices.

One embodiment of a method of the invention is a method for alleviating pulmonary hypertension by shunting the main pulmonary artery PA to the right atrium or atrial appendage (RAA). In this method, a right-to-right shunt from a region of higher pressure in the PA is connected to a region of lower pressure in the RAA. Doing so utilizes the high compliance of the RAA to "absorb" additional volume received from the shunt. The RAA is a naturally compliant reservoir. An additional benefit may arise from the fact that the RAA and the main PA are both inside the pericardium and, therefore, would contain any leaks resulting as a complication of an improperly seated shunt. Another benefit may be that the risk of puncturing the aorta is minimized.

Referring now to FIGS. 64-67 this procedure is detailed. FIG. 64 shows a first step in this method. Using a percutaneous delivery device 600, a puncture is made from the RAA to the PA, using a snare 602 as a guide. The delivery device 600 includes a needle 604 and a guidewire 606. The puncture is made using the needle 604.

The second step, as seen in FIG. 65, is to retract the needle 604.

The third step, shown in FIG. 66, involves crossing through the puncture made with the needle 604 with a stent sheath 608 deployed through the delivery device 600, and along the guidewire 606.

The final step is shown in FIG. 67 and involves deploying a shunt or stent of the invention.

Other installation method may be used to install the shunts and stents described herein. Discussion is now directed toward the location sites of the shunts of the invention and their resulting benefits.

Some applications of the invention are specific for PA shunting to mitigate pulmonary hypertension. For example, a connection may be made between the pulmonary artery in the superior vena cava will prevent elevated pressurization of the right heart and arteries yielding a combination of right heart failure and progressive pulmonary fibrosis. Connection to a compliant chamber such as the superior vena cava will decrease elevated pressures as a result of the systolic blood bolus.

This connection will also shunt blood away from the lungs, creating a low afterload resistance and hence lower right heart pressures with decreased load resistance. This configuration will enhance the volume of right heart and at the same time functioning to recirculate blood in lungs. A portion of the blood will be diverted from the pulmonary arteries at lungs, reinserted in the right atrium to be ejected into the pulmonary arteries again.

This strategy effectively substitutes right heart/right ventricle volume increase for decreasing pressure overload. It thus protects lungs from over pressure as well and slows progression of right heart and pulmonary microvascular disease. Therapeutic intervention such as this allows microvessels of heart and lungs to heal as pressures are dropped.

PA to PV

A connection made between the PA and the PV may be used to treat pulmonary hypertension or right hear failure or dysfunction. In order to reduce the total pulmonary vascular resistance and the afterload of the right ventricle, a shunt is created between the RPA and the RPV. Alternatively, the shunt could be placed between the LPA and the LPV.

PA to LAA

A connection could be made between the pulmonary artery and the left atrial appendage LAA, in order to treat pulmonary hypertension, right hear failure or dysfunction, or Afib. In order to reduce the total pulmonary vascular resistance and the afterload of the right ventricle, a shunt could be created between the PA and the LAA. An added benefit to the reduced right ventricular afterload is the washout of the LAA in those patients that are at risk of stroke.

SVC to RPA

A connection made between the RPA and the SVC may be used to treat pulmonary hypertension or right hear failure or dysfunction. In order to reduce the total pulmonary vascular resistance and the afterload of the right ventricle, a shunt is created between the RPA and the SVC. The method in which to do so are described in FIGS. 99-104.

Figure 99:
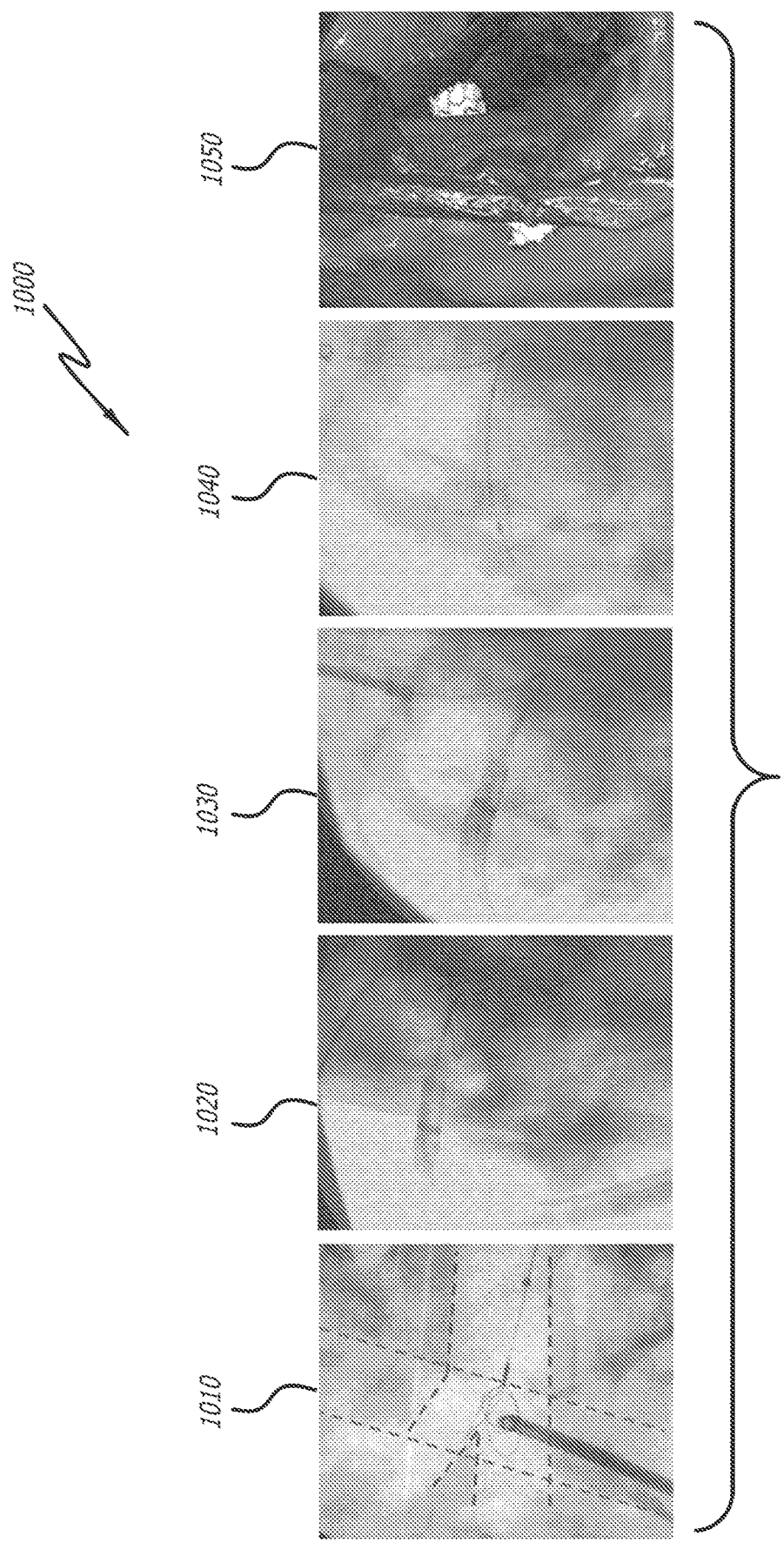
FIG. 99 is a diagrammatic overview of a method of the invention.

FIG. 99 shows an overview of a method 1000 of the invention. The method generally includes the steps of targeting the RPA 1010, crossing through the RPA to the SVC with a guidewire 1020, positioning the stent 1030, inflating the stent 1040, and removing the delivery system to establish the RPA to SVC shunt 1050.

FIGS. 100-104 show the procedure 1000 in more detail. Step 1100 involves the collection of pre-implant hemodynamics and includes the substeps of accessing the right IJ with a 10 Fr catheter sheath 1110. Next, at 1120, a Swan-Ganz catheter, for example, is floated into the LPA. Finally, at 1130, hemodynamic data is collected in "rest" and "leg raise" positions.

FIG. 101 shows the step 1200 of placing the target in the RPA. Step 1200 includes the substeps of first, at 1210, inserting a pigtail through the right IJ access. This may also include performing an angiogram of the SVC. Next, at 1220, the femoral vein is accessed with a 12 Fr sheath. Next at 1230, an arrow balloon catheter is floated to the RPA. The next substep 1240 involves inserting a 0.035" Amplatz Super Stiff GW. This is a preferred guidewire but is not to be construed as limiting. This disclaimer also applies to the other specific devices used in the method. Finally, at 1250, a Merit EnSnare device is inserted and positioned at the target site.

FIG. 102 shows the step 1300 of introducing the puncture system. First, at 1310, the femoral vein is accessed with a 12 Fr catheter sheath. Next, at 1320, a 0.035" guidewire is advanced to the SVC. Next, at 1330, an Agilis is tracked with a dilator over the guidewire GW into the SVC. Then, at 1340, the dilator is exchanged for a puncture system.

FIG. 103 shows the step 1400 of puncturing the SVC to the RPA. First, at 1410, the dilator tip is steered to target the puncture location and the tip angle and position are confirmed on the fluoro in the AP and lateral positions. Next, at 1420, RF is activated while advancing the micro catheter and RF wire together. Next, at 1430, it is confirmed that the snare has captured the guidewire. Next, at 1440, the snare is used on the guidewire and positioned proximal to the puncture site in the RPA.

FIG. 104 shows the shunt deployment step 1500. First, at 1510, a shunt is advanced with a delivery system over the guidewire. Next, at 1520, the shunt is centered across the puncture site. Finally, at 1530, the shunt is deployed and the delivery system is removed.

Of the shunts disclosed in this application, the shunts shown and described in FIGS. 88-98 have proven to perform with excellent results in this method. The shunts 720, 740 and 760 have upper flares 726, 746, and 766 that are longer than their counterpart bottom flares 728, 748 and 768, respectively. Good results have been achieved with the longer flares placed in the SVC and the shorter flares placed in the PA. The terms "upper" and "lower" are used herein only to describe their positions in the figures and not in the body in actual use.

PV to SVC

A shunt can be created between the PV and SVC to treat heart failure. Currently there are several intra-atrial shunts under evaluation in heart failure patients. In these patients, left atrial pressures are elevated causing fluid to back up in the lungs, and patients suffer from dyspnea or shortness of breath. The intra-atrial shunts divert flow from the LA to the RA.

In this disclosure it is proposed to shunt between the RPV and the SVC in order to reduce left atrial pressures. Due to the shunt location being in the SVC and LPV, this solution should have the added benefit of embolic protection.

Plurality of Shunts

Many heart failure patients suffer from pulmonary hypertension and resistant hypertension. It is therefore proposed that in certain patients, it may be ideal to place a plurality of shunts in multiple different locations. There may be a benefit to placing an RPA-SVC shunt as well as an atrial shunt in certain populations. The RPA-SVC shunt would help reduce RV afterload and the LA shunt would help reduce PVR while keeping LA pressure and LV filling pressure low. To the same effect, there may be a benefit to the combination of the RPA-VC, intra-atrial, and arteriovenous peripheral shunt in certain patients.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for treating a medical condition in a circulatory system of a human comprising:
   puncturing a superior vena cava and a pulmonary artery;
   connecting the superior vena cava and the pulmonary artery; and,
   diverting part of a blood flow from the pulmonary artery into the superior vena cava and allowing the blood flow into a right atrium of a heart.

2. The method according to claim 1, wherein the puncturing the pulmonary artery comprises puncturing a right pulmonary artery.

3. The method according to claim 1, wherein the puncturing of the pulmonary artery comprises puncturing a main pulmonary artery branch.

4. The method according to claim 1, wherein the medical condition is pulmonary hypertension.

5. The method according to claim 1, further comprising initially collecting pre-diversion hemodynamics test results.

6. The method according to claim 1, wherein puncturing the superior vena cava and the pulmonary artery further comprises activating and advancing radio frequency wire from the superior vena cava into the pulmonary artery.

7. The method according to claim 1, wherein connecting the superior vena cava and the pulmonary artery comprises deploying a shunt across a puncture site of the superior vena cava and the pulmonary artery.

8. The method according to claim 7, wherein the deploying the shunt comprises deploying a flared end of the shunt in the pulmonary artery.

9. The method according to claim 8, wherein the deploying the shunt comprises deploying a flared end of the shunt in the superior vena cava.

10. A method according to claim 7, wherein the shunt is a covered stent.

11. A method according to claim 7, wherein the shunt is a balloon expandable stent.

12. A method according to claim 7, connecting the superior vena cava and the pulmonary artery comprises creating either a spaced apart tubular connection or a flush connection between the superior vena cava and the pulmonary artery.

13. A method for treating a medical condition in a circulatory system of a human comprising:
   connecting a superior vena cava and a pulmonary artery by creating either a spaced apart tubular connection or a flush connection between the superior vena cava and the pulmonary artery; and,
   diverting part of a blood flow from the pulmonary artery into the superior vena cava and allowing the blood flow into a right atrium of a heart.

* * * * *